(12) United States Patent
McGrath

(10) Patent No.: US 9,364,501 B2
(45) Date of Patent: *Jun. 14, 2016

(54) CHLORITE IN THE TREATMENT OF NEURODEGENERATIVE DISEASE

(75) Inventor: Michael S. McGrath, Burlingame, CA (US)

(73) Assignee: The Regents of the University of California, Oakland, CA (US)

(*) Notice: Subject to any disclaimer, the term of this patent is extended or adjusted under 35 U.S.C. 154(b) by 193 days.

This patent is subject to a terminal disclaimer.

(21) Appl. No.: 13/458,954

(22) Filed: Apr. 27, 2012

(65) Prior Publication Data

US 2012/0295296 A1 Nov. 22, 2012

Related U.S. Application Data

(60) Continuation of application No. 12/900,361, filed on Oct. 7, 2010, which is a continuation of application No. 11/378,987, filed on Mar. 17, 2006, now Pat. No. 8,029,826, which is a division of application No. 11/042,816, filed on Jan. 24, 2005, now Pat. No. 7,105,183.

(60) Provisional application No. 60/541,576, filed on Feb. 3, 2004.

(51) Int. Cl.
  *A61K 33/20* (2006.01)
  *A61K 33/00* (2006.01)
  *A61K 33/40* (2006.01)

(52) U.S. Cl.
  CPC ............ *A61K 33/20* (2013.01); *A61K 33/00* (2013.01); *A61K 33/40* (2013.01); *Y10S 514/879* (2013.01); *Y10S 514/885* (2013.01)

(58) Field of Classification Search
  CPC .... A61K 33/00; A61K 33/20; Y10S 514/879; Y10S 514/885
  USPC ............ 424/613, 615, 661, 662, 663, 665; 514/885
  See application file for complete search history.

(56) References Cited

U.S. PATENT DOCUMENTS

| | | | |
|---|---|---|---|
| 4,507,285 A | 3/1985 | Kuhne | |
| 4,576,945 A | 3/1986 | Sanders | |
| 4,725,437 A | 2/1988 | Kuhne | |
| 5,051,414 A | 9/1991 | Domaile et al. | |
| 5,855,922 A | 1/1999 | Danner et al. | |
| 5,877,222 A | 3/1999 | McGrath | |
| 6,086,922 A | 7/2000 | Kuhne | |
| 6,099,855 A | 8/2000 | Mullerat et al. | |
| 7,105,183 B2 | 9/2006 | McGrath | |
| 2001/0036631 A1 | 11/2001 | McGrath et al. | |
| 2003/0130350 A1 | 7/2003 | Ramesh et al. | |
| 2003/0130357 A1 | 7/2003 | Ramesh et al. | |
| 2003/0158262 A1 | 8/2003 | Ramesh et al. | |
| 2003/0175832 A1 | 9/2003 | Marton et al. | |
| 2005/0129784 A1 | 6/2005 | Kuehne | |
| 2005/0181068 A1 | 8/2005 | McGrath | |
| 2006/0159775 A1 | 7/2006 | McGrath | |
| 2011/0053186 A1 | 3/2011 | McGrath | |

FOREIGN PATENT DOCUMENTS

| | | |
|---|---|---|
| JP | 2001-078775 | 3/2001 |
| WO | WO 99/17787 | 4/1999 |
| WO | WO 99/21542 | 5/1999 |
| WO | WO 01/40517 | 6/2001 |
| WO | WO 03/048773 | 6/2003 |

OTHER PUBLICATIONS

Inorganic Ventures, "Certificate of Analysis for 1000 μg/ml Chlorite Solution", 2008, 2 pgs.
Product Insert: Data and instruction for the Use of Immunokine WF10 (TCDO) I.v.Solution for Intravenous Infusion, OXO Chemie, Published approximately 1997.
Shahangian, et al, "The reaction of chloroperoxidase with chlorite and chlorine dioxide", J Biol Chem, 1981, 256:6034-40.
Steffen, et al, "Chlorate poisoning: mechanism of toxicity", Toxicology, 1993, 84:217-31.
Tissot, et al., Anti-inflammatory properties of a novel wound healing and immunomodulating agent, tetrachlorodecaoxygen complex (TCDO). Agents Actions. Nov. 1990;31(3-4):368-74.
Liu, et al., "Risk factor analysis and prevention of Alzheimer's disease", Chinese Archives of Traditional Chinese Medicine, 2002, 20:744-5.
Adamson et al; Rate and Severity of HIV-Associated Dementia (Had): 1999 *Mol. Med.* (5) 98-109.
Liu et al. Analysis of human immunodeficiency virus type 1 gp160 sequences from a patient with HIV dementia: evidence for monocyte trafficking into brain. *J. Neurovirol.* 2000,6(suppl 1): S70-81.
Fischer-Smith et al. CNS invasion by CD14+/CD16+ peripheral blood-derived monocytes in HIV dementia: perivascular accumulation and reservoir of HIV infection, *J. Neurovirol*, 2001. 7:528-541.
McGrath et al. Development of WF10, a novel macrophage-regulating agent. *Curr. Opin. Investig. Drugs* 2002,3:365-373.
Dimethaid Research Inc.—WF10, Immune Regulation, p. 1-2, http://www.dimethaid.com/products/wf10.asp.
McGrath, et al. Differential effects on innate versus adaptive immune responses by WF10. Cell Immunol. Jun. 2004; 229(2): 149-58.
Srisupundit, et al. The efficacy of chemically-stabilized chlorite-matrix (TCDO) in the management of late postradiation cystitis. J Med Assoc Thai. Aug. 1999; 82(8): 798-802.
Ennen, et al. Inactivation of HIV infectivity by the chlorite-oxygen reaction product tetrachlorodecaoxygen. AIDS. Sep. 1993; 7(9): 1205-12.
Kempf SR., et al. Comparative study on the effects of chlorite oxygen reaction product TCDO (tetrachlorodecaoxygen) and sodium chlorite solution (NaClO2) with equimolar chlorite content on bone marrow and peripheral blood of BDIX rats. Drugs Exp Clin Res. 1993; 19(4): 165-74.

(Continued)

*Primary Examiner* — John Pak
(74) *Attorney, Agent, or Firm* — Shweta Chandra; Carol L. Francis; Bozicevic, Field & Francis, LLP

(57) ABSTRACT

The invention features methods of treating a macrophage-associated neurodegenerative disease such as amyotrophic lateral sclerosis (ALS), Alzheimer's disease (AD), or multiple sclerosis (MS) in a subject by administering chlorite in an amount effective to decrease blood immune cell activation. The invention also features methods of monitoring therapy by assessing blood immune cell activation before and after therapy.

9 Claims, 8 Drawing Sheets

(56) References Cited

OTHER PUBLICATIONS

Habermann E, et al. [Oxoferin and sodium chlorite—a comparison] Klin Wochenschr. Jan. 4, 1989;67(1):20-5. German. , PMID: 2921839.
Elstner EF [Heme activated oxidations using the chlorite-oxygen complex "TCDO" (Oxoferin)—an overview] Z Naturforsch [C]. Nov.-Dec. 1988;43(11-12):893-902. German., PMID: 3245879.
Weise K. et al. Clinical experiences with tetrachlorodecaoxide in the local treatment of difficult-to-heal wounds, Aktuelle Traumatol. Oct. 1988;18(5):219-25.
Karrow NA. et al. Evaluation of the immunomodulatory effects of the disinfection by-product, sodium chlorite, in female B6C3F1 mice: a drinking water study.Drug Chem Toxicol. Aug. 2001;24(3):239-58.
Weislow OS. et al. Suppression of extablished Friend virus leukemia by statolon: potentiation of statolon's leukemosuppressive activity by chlorite-oxidized oxyamylose. Infect Immun. Jan. 1975;11(1):129-36.
Billiau A. et al. Antiviral activity of chlorite-oxidized oxyamylose, a polyacetal carboxylic acid. J Virol. Mar. 1970;5(3):321-8.
Akiyama et al. Inflammation and Alzheimer's disease, Neurobiol Aging. May-Jun. 2000; 21(3):383-421.
Alexianu et al. Immune reactivity in a mouse model of familial ALS correlates with disease progression, Neurology. Oct. 9, 2001; 57(7):1282-9.
Anderson et al. A novel phenotype for an activated macrophage: the type 2 activated macrophage. J Leukoc Biol. Jul. 2002; 72(1):101-6.
Appel et al. Evidence for autoimmunity in amyotrophic lateral sclerosis, *J. Neurol. Sci*, 1993. 118:169-174.
Cremer et al. Antibody titers to coxsackieviruses in amyotrophic lateral sclerosis, *N. Engl. J. Med*, 1976. 295(2):107-108. (Letter).
Diesing et al. HIV-1-associated dementia: a basic science and clinical perspective, *AIDS Read*, 2002. 12:358-368.
Engelthardt .et al. IgG reactivity in the spinal cord and motor cortex in amyotrophic lateral sclerosis, *Arch. Neurol*. 1990. 47:1210-1216.
Fiala et al. Cyclooxygenase-2-positive macrophages infiltrate the Alzheimer's disease brain and damage the blood-brain barrier, *Eur. J. Clin. Invest*. 2002,32:360-371.
Giese et al. Differential effects on innate versus adaptive immune responses by WF10, Cell Immunol. Jun. 2004;229(2):149-58.
Glass et al. Immunocytochemical quantitation of human immunodeficiency virus in the brain: correlations with dementia. *Ann. Neurol*, 1995. 38:755-762.
Hansen et al. High-dose stabilized chlorite matrix WF10 prolongs cardiac xenograft survival in the hamsterto-rat model without inducing ultrastructural or biochemical signs of cardiotoxicity. Pharmacol Toxicol. Aug. 2001; 89(2):92-5.
Hayashi et al. Pathological study of the diffuse myelin pallor in the anterolateral columns of the spinal cord in amyotrophic lateral sclerosis, *J. Neurol. Sci*. 2001,188:3-7.
Hensley et al. Temporal patterns of cytokine and apoptosis-related gene expression in spinal cords of the G93A-SOD1 mouse model of amyotrophic lateral sclerosis. *J. Neurochem*, 2002. 82:365-374.
Hirsch et al. The role of glial reaction and inflammation in Parkinson's disease. *Ann. N.Y. Acad. Sci*, 2003. 991:214-228.
Janssen et al. Nomenclature and research case definitions of neurologic manifestatations of human immunodeficiency virus-type 1 (HIV-1) infection. *Neurology*. 1991,41:778-785.
Kemp et al. Immunosuppression in xenotransplantation with Wf10. Pharmacol Toxicol. Jun. 2002;90(6):346-8.
Kemp et al. WF10 in xenotransplantation-a potential new approach Transplant Proc. Aug. 2000;32(5):1018-9.
Klaustermeyer et al. Quantitative immunoglobulins and IgG subclasses in patients with corticosteroid-dependent reversible airway obstruction. *Ann. Allergy*. 1989,63:327-330.
Kott et al. Cell-mediated immunity to polio and HLA antigens in amyotrophic lateral sclerosis. *Neurology*. 1979,29:1040-1044.
Lehrich et al. Neutralizing antibodies to poliovirus and mumps virus in amyotrophic lateral sclerosis. *J. Neurol. Sci*. 1974,23:537-540.

MacGowan et al. An ALS-like syndrome with new HIV infection and complete response to antiretroviral therapy. *Neurology*. 2001. 57:1094-10.
Marshall et al. Cytokine dysregulation associated with exam stress in healthy medical students. *Brain Behav. Immun*. 1998,12:297-307.
McArthur et al. Dementia in AIDS patients: incidence and risk factors. *Neurology*, 1993, 43:2245-2252.
McGeer et al. The importance of inflammatory mechanisms in Alzheimer disease. *Exp. Gerontol*. 1998, 33:371-378.
McGeer et al. Inflammatory processes in amyotrophic lateral sclerosis. *Muscle Nerve*. 2002,26:459-470.
McGrath et al. Effect of WF10 (TCDO) on antigen presentation. *Transplant. Proc*. 1998,30:4200-4204.
McGrath et al. Balanced macrophage activation hypothesis: a biological model for development of drugs targeted at macrophage functional states. *Pathobiology*. 1999, 67:277-81.
Minagar et al. The role of macrophage/microglia and astrocytes in the pathogenesis of three neurologic disorders: HIV-associated dementia, Alzheimer disease, and multiple sclerosis. *J. Neurol. Sci*. 2002,202:13-23.
Mizutani et al. Sensorimotor demyelinating neuropathy with IgM antibody against gangliosides GD1a, GT1b and GM3. *J. Neurol. Sci*. 2001, (188) 9-11.
Morgan et al. Clinical significance of IgG subclass deficiency. *Arch. Dis. Child*. 1988,63:771-773.
Moulignier et al. Reversible ALS-like disorder in HIV infection. *Neurology*. Sep. 2001, 57:995-1001.
Nguyen et al. Induction of proinflammatory molecules in mice with amyotrophic lateral sclerosis: no requirement for proapoptotic interleukin-1beta in neurodegeneration. *Ann. Neurol*. 2001, 50:630-639.
Nottet et al. Mechanisms for the transendothelial migration of HIV-1-infected monocytes into brain. *J. Immunol*. 1996.156:1284-1295.
Obal et al. Recruitment of activated microglia cells in the spinal cord of mice by ALS IgG. *Neuroreport*. 2001,12:2449-2452.
Ono et al. Increased interleukin-6 of skin and serum in amyotrophic lateral sclerosis. *J. Neurol. Sci*. 2001,187:27-34.
Ostermeyer-Shoaib et al. IgG subclass deficiency in amyotrophic lateral sclerosis. *Acta Neurol Scand*. 1993,87:192-194.
Raffanti et al. Randomized, double-blind, placebo-controlled trial of the immune modulator WF10 in patients with advanced AIDS. *Infection*. Jul.-Aug. 1998;26(4):202-7.
Power et al. Neuroimmune and neurovirological aspects of human immunodeficiency virus infection. *Adv. Virus. Res*. 2001.56:389-433.
Provinciali et al. Immunity assessment in the early stages of amyotrophic lateral sclerosis: a study of virus antibodies and lymphocyte subsets. *Acta. Neurol. Scand*. 1988,78:449-454.
Pulliam et al. Unique monocyte subset in patients with AIDS dementia. *Lancet*. 1997,349:692-695.
Schempp et al. Chlorite-hemoprotein interaction as key role for the pharmacological activity of the chlorite-based drug WF10. ArzneimForschDrugRes. 2001;51(II):554-62.
Schiffer et al. Reactive astrogliosis of the spinal cord in amyotrophic lateral sclerosis. *J. Neurol. Sci*. 1996,139(suppl):27-33.
Smits et al. Role of macrophage activation in the pathogenesis of Alzheimer's disease and human immunodeficiency virus type 1-associated dementia. *Eur. J. Clin. Invest*. 2000,30:526-535.
Sola et al. New insights into the viral theory of amyotrophic lateral sclerosis: study on the possible role of Kaposi's sarcoma-associated virus/human herpesvirus 8. *Eur. Neurol*. 2002,47:108-112.
The Dana Consortium on Therapy for HIV Dementia and Related Cognitive Disorders. Clinical confirmation of the American Academy of Neurology algorithm for HIV-1-associated cognitive/motor disorder. *Neurology*. 1996,47:1247-1253.
Tikka et al. Minocycline, a tetracycline derivative, is neuroprotective against excitotoxicity by inhibiting activation and proliferation of microglia. *J. Neurosci*. 2001, 21:2580-2588.
Troost et al. Lymphocytic infiltration in the spinal cord of patients with amyotrophic lateral sclerosis. *Clin. Neuropathol*. 1989, 8:289-294.
Van Den Bosch et al. Minocycline delays disease onset and mortality in a transgenic model of ALS. *Neuroreport*. 2002, 13:1067-1070.

(56) References Cited

OTHER PUBLICATIONS

Veerasarn et al. Reduced recurrence of late hemorrhagic radiation cystitis by WF10 therapy in cervical cancer patients: a multicenter, randomized, two-arm, open-label trial. *Radiother Oncol.* Nov. 2004; 73(2):179-85.
Williams et al. Proliferating cellular nuclear antigen expression as a marker of perivascular macrophages in simian immunodeficiency virus encephalitis. *Am. J. Pathol.* 2002, 161:575-585.
Zhang et al. Evidence for systemic immune system alterations in sporadic amyotrophic lateral sclerosis (sALS). *J Neuroimmunol.* Feb. 2005; 159(1-2):215-24. Epub Nov. 26, 2004.
Jones-London. What's old is new again—antibiotic protects nerves by removing excess glutamate. 2005, Retrieved from the internet on Nov. 29, 2005. URL: http://www.ninds.nih.gov/news_and_events/news_articles/news_article_ALS_ceftriaxone.htm.
Miller, T. et al., "Treating Neurodegenerative Diseases with Antibiotics," Science, vol. 307, pp. 361-362 (Jan. 21, 2005).
Rothstein, J.D. et al., "Beta-lactam antibiotics," Science, vol. 307, pp. 361-362 (Jan. 21, 2005).
Ziegler, T. Doubling up . . . common dietary supplement with an antibiotic to treat Lou Gehrig's Disease. Jan. 31, 2003. Retrieved from the internet on Nov. 29, 2005. URL: http://www.ninds.nih.gov/news_and_events/news_articles/news_article_als_combination_treat.
Zhu, S. et al., "Minocycline inhibits cytochrome c release and delays progression of amyotrophic lateral sclerosis in mice," Nature, vol. 417, pp. 74-78 (May 2, 2002).
Habermann, E., et al. "Oxoferin and sodium chlorite-a comparison," Klin Wochenschr, vol. 67(1), Jan. 1989, pp. 20-25 (English Translation).
Sorg, O. Oxidative stress: a theoretical model or a biological reality? C R Biol. Jul. 2004;327(7):649-62.
Smith, et al. The redox chemistry of the Alzheimer's disease amyloid beta peptide. Biochim Biophys Acta. Aug. 2007;1768(8):1976-90.
Zhu, et al. Oxidative stress signalling in Alzheimer's disease. Brain Res. Mar. 12, 2004;1000(1-2):32-9.
European Examiner's Report for Application No. 05722556.7 dated Nov. 15, 2010.
BioMaxx—Immunokine. (Therapy System Sahintro Matrix) http:biomaxx-sys.com/immunokine.html (2011).
BIOSIS abstract, accession No. 1994:163800. 1994.
BIOSIS abstract, accession No. 1994:488901. 1994.
European Search Report dated Nov. 17, 2008, for EP05722556.7, 3pp.
International Search Report & Written Opinion dated Feb. 9, 2006, for PCT/US2005/002469, 13pp.
MEDLINE abstract, accession No. 2003039765. 2003.
Remington: The Science and Practice of Pharmacy, 21st Edition, Lippincott Williams & Wilkins, chapter 41, p. 802, 2005.
United States Pharmacopeia and National Formulary (USP32-NF27). Chapters <71> Sterility Tests and <1211> Sterilization. Rockville, MD: United States Pharmacopeia Convention. Dec. 1, 2009.
United States Pharmacopeia and National Formulary (USP32-NF27). Chapter <1> Injections. Rockville, MD: United States Pharmacopeia Convention. Dec. 1, 2009.
United States Pharmacopeia and National Formulary (USP29-NF24). Chapter <1231> Water for Pharmaceutical Purposes. Rockville, MD: United States Pharmacopeia Convention. 2006.
Kaczur, et al., "Chlorine Oxygen Acids and Salts, Chlorous Acid, Chlorites, and Chlorine Dioxide", Kirk-Othmer Encyclopedia of Chemical Technology, Wiley Library, 2000, 26 Pages.
Qian, et al., "A clean production process of sodium chlorite from sodium chlorate", Journal of Cleaner Production, 15(10), pp. 920-926, 2007.

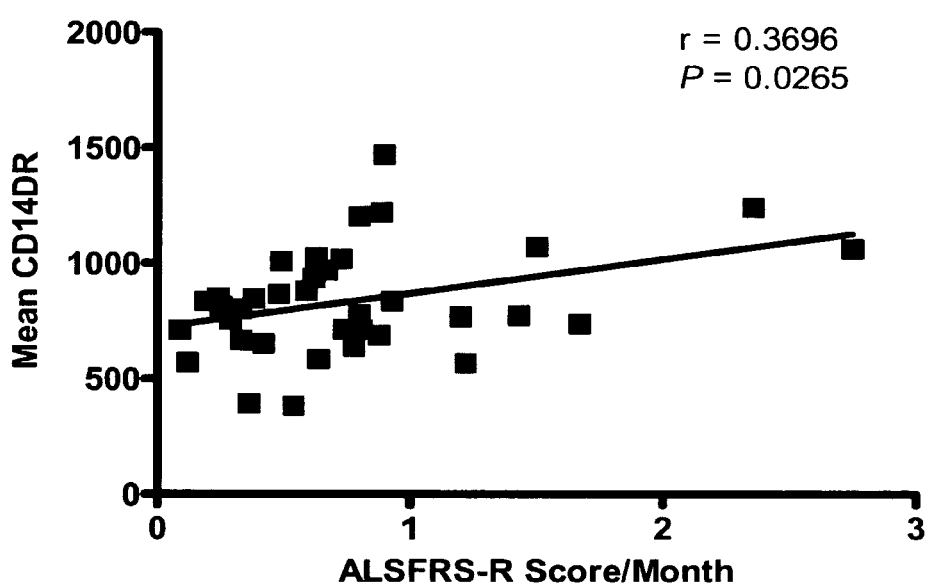

CHLORITE IN THE TREATMENT OF NEURODEGENERATIVE DISEASE

CROSS REFERENCES TO RELATED APPLICATIONS

This application is a continuation of U.S. patent application Ser. No. 12/900,361 filed on Oct. 7, 2010, currently pending, which is a continuation of U.S. patent application Ser. No. 11/378,987 filed on Mar. 17, 2006 issued as U.S. Pat. No. 8,029,826 on Oct. 4, 2011, which is a divisional of U.S. patent application Ser. No. 11/042,816 filed on Jan. 24, 2005 issued as U.S. Pat. No. 7,105,183 on Sep. 12, 2006, which application claims the benefit of U.S. provisional application Ser. No. 60/541,576, filed Feb. 3, 2004, which application is incorporated herein by reference in its entirety.

GOVERNMENT RIGHTS

This invention was made with government support under grant no. CA66529 awarded by the National Institutes of Health. The government has certain rights in the invention.

FIELD OF THE INVENTION

The present invention generally relates to the use of chlorite in treatment of neurodegenerative disease, particularly a neurodegenerative disease characterized by pathologic macrophages, such as amyotrophic lateral sclerosis (ALS), multiple sclerosis (MS), HIV-associated neurological disorders, or Alzheimer's disease (AD).

BACKGROUND OF THE INVENTION

Neurodegenerative diseases are generally characterized by a degeneration of neurons in either the brain or the nervous system of an individual. Amyotrophic lateral sclerosis (ALS), Alzheimer's disease (AD), and multiple sclerosis (MS) fall within this category. These diseases are debilitating, the damage that they cause is often irreversible, and the outcome in a number of cases is fatal.

ALS is characterized by gradual degeneration of motor neuron cells in the spinal cord and brain, which ultimately leads to progressive weakness and paralysis of muscle and death. ALS occurs in two clinically indistinguishable forms, referred to as a sporadic form and a familial form. The pathogenesis of ALS is incompletely understood, although different hypotheses have been suggested, including mitochondria dysfunction, mutation in the superoxide dismutase gene, and defects in neuronal glutamate transport. Autoimmunity has also been hypothesized to be involved in ALS pathogenesis (Appel et al. 1993. *J. Neurol. Sci.* 118:169-174). In addition, several recent studies have suggested that the immune system may be actively involved in the disease process of ALS, with observations of activated microglia, IgG deposits, increased FcR expression, and dysregulation of cytokine expression in the spinal cord of ALS patients (Troost et al. 1989. *Clin. Neuropathol.* 8:289-294; Engelthardt et al. 1990. *Arch. Neurol.* 47:1210-1216; Schiffer et al. 1996. *J. Neurol. Sci.* 139 (suppl):27-33; Hayashi et al. 2001 *J. Neurol. Sci.* 188:3-7.9-12).

Recent clinical and pathological studies have shown that involvement outside the motor neuron system is relatively common in Amyotrophic Lateral Sclerosis (ALS) (Hayashi et al. 2001, supra; Obal et al. 2001 *Neuroreport.* 12:2449-2452; Sola et al. 2002 8. *Eur. Neurol.* 47:108-112; Ono et al. 2001 *J. Neurol. Sci.* 187:27-34; Alexianu et al. 2001 *Neurology.* 57:1282-1289.). Microglia/macrophage activation and inflammatory response have been implicated in ALS disease progression (Appel et al. 1993, supra; Engelthardt et al. 1990, supra; Hayashi et al. 2001 supra; Obal et al. 2001 Neuroreport. 12:2449-2452; McGeer et al. 2002 *Muscle Nerve.* 26:459-47028, 29). However, few studies to date have explored the status of the systemic immune response in ALS. Despite intensive investigation, ALS has no known cause or effective therapy.

Retroviral infection has recently been implicated in the pathogenesis of an ALS-like syndrome in patients with HIV-associated disease. Moulignier et al. (Reversible ALS-like disorder in HIV infection. *Neurology.* 57:995-1001) recently reported the outcome of six HIV-1-infected patients with a neurologic disorder mimicking ALS and all those patients stabilized or improved with antiretroviral therapy. MacGrowen et al. (2001. An ALS-like syndrome with new HIV infection and complete response to antiretroviral therapy. *Neurology.* 57:1094-10) also reported a dramatic clinical response to antiretroviral therapy in an ALS-like syndrome with new HIV infection.

Approximately one-quarter of individuals with AIDS develop neuropathological symptoms. Infection by HIV-1 causes inflammation within the brain and neuronal degeneration (Power et al. 2001 *Adv. Virus. Res.* 56:389-433), resulting in HIV-associated dementia (HAD) or the less severe minor cognitive and motor disorders (Janssen et al. 1991 Report of a Working Group of the American Academy of Neurology AIDS Task Force. *Neurology.* 41:778-785; McArthur et al. 1993 Multicenter AIDS Cohort Study. *Neurology.* 43:2245-2252; The Dana Consortium. 1996. Clinical confirmation of the American Academy of Neurology algorithm for HIV-1-associated cognitive/motor disorder. The Dana Consortium on Therapy for HIV Dementia and Related Cognitive Disorders. *Neurology.* 47:1247-1253.).

The mechanisms underlying HIV-associated neuronal injury are incompletely understood. Various studies have suggested that monocytes/macrophage activation may play a significant role in the pathogenesis of many neurological diseases (Smits et al. 2000 *Eur. J. Clin. Invest.* 30:526-535; Fiala et al. 2002 *Eur. J. Clin. Invest.* 32:360-371; Minagar et al. 2002 The role of macrophage/microglia and astrocytes in the pathogenesis of three neurologic disorders: HIV-associated dementia, Alzheimer disease, and multiple sclerosis. *J. Neurol. Sci.* 202:13-23), including HIV-associated neurologic disorders (Pulliam et al. 1997 *Lancet.* 349:692-695; Diesing et al. 2002 *AIDS Reader.* 12:358-368). Indeed, the best pathological correlate for HIV-associated neurologic disorders, especially HAD, is the number of activated mononuclear phagocytes (perivascular and parenchymal blood-derived macrophages and microglia), not the absolute levels of virus in brain per se (Glass et al. 1995 *Ann. Neurol.* 38:755-762; Adamson et al. 1999 *Mol. Med.* 5:98-109). Similar findings have been reported for simian AIDS related encephalopathy (SIVE) (Williams et al. 2002 *Am. J. Pathol.* 161:575-585). Macrophage activation has been reported in spinal cords of patients with ALS disease (Appel et al. 1993, supra; Engelthardt et al. 1990, supra; Obal et al. 2001, supra; McGeer et al. 2002, supra), although the role of macrophage activation in ALS pathogenesis has not been previously determined.

Studies on blood from patients with HAD (Liu et al. 2000 *J. Neurovirol.* 6(suppl 1): S70-81) and monkeys with SIVE (Williams et al. 2002 *Am. J. Pathol.* 161:575-585) have shown a direct relationship between the presence of activated blood macrophages and central nervous system (CNS) disease.

These activated macrophages are thought to mediate blood brain barrier (BBB) breakdown and directly contribute to CNS pathogenesis.

Alzheimer's disease (AD) is the most common form of dementia among the elderly. Various studies have suggested that macrophage activation may be involved in AD (see, e.g., WO 99/21542). Currently the only definite way to diagnose AD is by post-mortem autopsy to assess the presence of amyloid plaques and tangles in brain tissue. Thus, AD diagnosis is generally a diagnosis of "possible" or "probable" AD. At specialized centers, doctors can diagnose AD correctly up to 90 percent of the time. Several tools are used to diagnose "probable" AD, including medical history, analysis of blood urine, or spinal fluid, to rule out other causes (e.g., thyroid deficiencies, infectious disease, etc.), brain scans, and neuropsychological tests to asses memory, problem solving, attention, counting, and language.

Multiple sclerosis (MS) is a chronic disease that is characterized by "attacks," during which areas of white matter of the central nervous system, known as plaques, become inflamed. Inflammation of these areas of plaque is followed by destruction of myelin, the fatty substance that forms a sheath or covering that insulates nerve cell fibers in the brain and spinal cord. Myelin facilitates the smooth, high-speed transmission of electrochemical messages between the brain, spinal cord, and the rest of the body. Damage to the myelin sheath can slow or completely block the transmission of these electrochemical messages, which can result in diminished or lost bodily function.

The most common course of MS manifests itself as a series of attacks, which are followed by either complete or partial remission, during which the symptoms lessen only to return at some later point in time. This type of MS is commonly referred to as "relapsing-remitting MS." Another form of MS, called "primary-progressive MS," is characterized by a gradual decline into the disease state, with no distinct remissions and only temporary plateaus or minor relief from the symptoms. A third form of MS, known as "secondary-progressive MS," starts as a relapsing-remitting course, but later deteriorates into a primary-progressive course of MS.

The symptoms of MS can be mild or severe, acute or of a long duration, and may appear in various combinations. These symptoms can include vision problems such as blurred or double vision, red-green color distortion, or even blindness in one eye, muscle weakness in the extremities, coordination and balance problems, muscle spasticity, muscle fatigue, paresthesias, fleeting abnormal sensory feelings such as numbness, prickling, or "pins and needles" sensations, and in the worst cases, partial or complete paralysis. About half of the people suffering from MS also experience cognitive impairments, such as for example, poor concentration, attention, memory and/or judgment. These cognitive symptoms occur when lesions develop in those areas of the brain that are responsible for information processing.

Despite the progress in the field, there remains a need for a therapy for treatment of ALS and MS, including alleviation of symptoms of these diseases. The present invention addresses this need.

LITERATURE

The following references, as well as those in the Bibliography and cited throughout, may be of interest: Akiyama et al. 2000 *Neurobiol. Aging.* 21:383-421; Anderson et al. 2002. *J. Leukoc. Biol.* 72:101-106; Cremer et al. 1976. *N. Engl. J. Med.* 295:107-108. (Letter); Fischer-Smith et al. 2001. *J. Neurovirol.* 7:528-541; Giese et al. Cell Immunol. 2004 June; 229(2):149-58; Hansen et al. Pharmacol Toxicol. 2001 August; 89(2):92-5; Hensley et al. 2002. *J. Neurochem.* 82:365-374; Hirsch et al. 2003. *Ann. N.Y. Acad. Sci.* 991:214-228; Kemp et al. Pharmacol Toxicol. 2002 June; 90(6):346-8; Kemp et al. Transplant Proc. 2000 August; 32(5):1018-9; Klaustermeyer et al. 1989. *Ann. Allergy.* 63:327-330; Kott et al. 1979. *Neurology.* 29:1040-1044; Lehrich et al. 1974. *J. Neurol. Sci.* 23:537-540; Marshall et al. 1998. *Brain Behav. Immun.* 12:297-307; McGeer et al. 1998. *Exp. Gerontol.* 33:371-378; Morgan et al. 1988. *Arch. Dis. Child.* 63:771-773; Nottet et al. 1996. *J. Immunol.* 156:1284-1295; Provinciali et al. 1988. *Acta. Neurol. Scand.* 78:449-454; Nguyen et al. 2001 *Ann. Neurol.* 50:630-639; Ostermeyer-Shoaib et al. 1993 *Acta Neurol Scand.* 87:192-194; Raffanti et al. Infection. 1998 July-August; 26(4):202-7; Schempp et al. Arzneimittelforschung. 2001; 51(7):554-62; Tikka et al. 2001. *J. Neurosci.* 21:2580-2588; Veerasarn et al. Radiother Oncol. 2004 November; 73(2):179-85. and Van Den Bosch et al. 2002. *Neuroreport.* 13:1067-1070.

See also: McGrath et al. 2002 *Curr. Opin. Investig. Drugs* 3:365-373; McGrath et al. 1999 *Pathobiology.* 67:277-81; McGrath et al. 1998 *Transplant. Proc.* 30:4200-4204; Giese et al. 2004 June; 229(2):149-58; Zhang et al. *J Neuroimmunol.* 2005 February; 159(1-2):215-24. Epub 2004 Nov. 26.

Also see: U.S. Pat. Nos. 4,725,437; 5,877,222; 6,086,922; and U.S. Publication Nos. 20030175832; 20030158262; 20030130357; and 20030130350.

SUMMARY OF THE INVENTION

The invention features methods of treating a macrophage-associated neurodegenerative disease such as amyotrophic lateral sclerosis (ALS), Alzheimer's disease (AD), or multiple sclerosis (MS) in a subject by administering chlorite in an amount effective to decrease blood immune cell activation. The invention also features methods of monitoring therapy by assessing blood immune cell activation before and after therapy.

BRIEF DESCRIPTION OF THE DRAWINGS

The invention is best understood from the following detailed description when read in conjunction with the accompanying drawings. Included in the drawings are the following figures:

FIGS. 2a-2b are graphs showing analyses of macrophage activation defined by CD14 co-expression of HLA-DR in patients with ALS. FIG. 2a is a graph showing a negative correlation of macrophage activation with ALSFRS-R scores in patients with ALS (Pearson r=−0.3424, P=0.0409). FIG. 2b is a graph showing a positive correlation of levels of HLA-DR on ALS CD14 cells with the rate of disease progression (ALSFRS-R score change per month) (Pearson r=0.3696, P.=0.0265).

FIG. 3a is a graph showing that significantly lower levels of serum-IgG were found in ALS patients with severe impairment compared to normal controls (P<0.05), but with no difference between patients with milder impairment and normal controls. FIG. 3b is a graph showing levels of serum-IgM in patients with milder impairment were significantly higher than normal controls (P<0.01), but with no difference between patients with severe impairment and normal controls.

Figure 1:
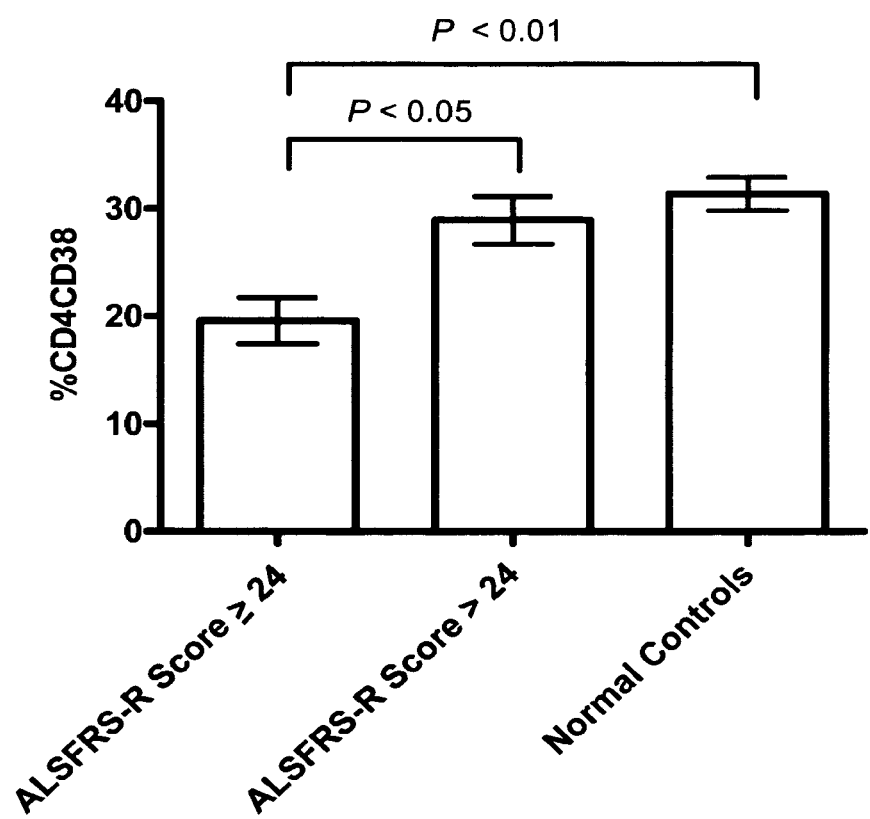
FIG. 1 is a graph showing the relationship of the revised ALS Functional Rating Score (ALSFRS-R) to CD4 T-cell co-expression of the activation antigen CD38 in ALS patients. Patients with ALS were divided into two groups based on a score of 24, the midpoint of the ALSFRS-R scale. The CD4 activation marker CD38 was significantly lower in patients with severe impairment (ALSFRS-R score of 0-24, n=10) compared to normal controls (P<0.01) and patients with milder impairment (ALSFRS-R score >24, n=26) (P<0.05), but no difference was found between normal controls and patients with milder impairment.

Before the present invention is described in more detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a chlorite matrix" includes a plurality of such chlorite matrices and reference to "the composition" includes reference to one or more compositions and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

Overview

The invention is based on the discovery that administration of WF10, which comprises chlorite (e.g., in the form of tetrachlorodecaoxygen (TCDO)) as its active ingredient, provides for treatment of patients having amyotrophic lateral sclerosis (ALS) and for treatment of patients having multiple sclerosis (MS). Without being held to theory, chlorite provides for a decrease in activated blood immune cells (e.g., activated macrophages), which are elevated in ALS and MS patients and contribute to ALS and MS disease pathogenesis. Further, since Alzheimer's disease (AD) is similarly characterized as being associated with activated blood immune cells in a manner that parallels ALS, AD is also amenable to treatment by administration of WF10. The invention is thus applicable to treatment of neurodegenerative diseases associated with activated blood immune cells, particularly with proliferating or inappropriate activated macrophages.

Definitions

A "neurodegenerative disease" refers to a central nervous system characterized by progressive, normally gradual, loss of functional neural tissue. Of particular interest in the present invention is the treatment of neurodegenerative diseases in which that affected patient has activated blood immune cells, particularly with proliferating or inappropriate activated macrophages. Reference to a "non-diseased" individual generally means an individual who is not diagnosed as having, or is not suspected of having, the relevant neurodegenerative disease. Reference to a "diseased" individual generally means an individual who has been diagnosed as having, or who is suspected of having, the relevant neurodegenerative disease. Exemplary neurodegenerative diseases include amyotrophic lateral sclerosis, multiple sclerosis, and pathogen-mediated or pathogen-associated neural diseases or symptoms (such as viral infection, e.g., HIV infection).

As used herein, the terms "macrophage" and "monocyte" are used interchangeably, as it is understood that in the art the term "monocyte" is often used to describe a circulating mononuclear cell that expresses the CD14 cell surface marker, and when in a tissue this cell is also classified as a macrophage.

An "abnormal macrophage" or "activated circulating monocyte" or "activated monocyte" as used interchangeably herein denotes a monocyte which expresses CD14 (i.e., CD14+) and which expresses an elevated level of HLA-DR, the major histocompatibility antigen class II, and/or which expresses CD16 (i.e., CD16+). Generally, abnormal macrophages are found in peripheral blood but they may also be found in other biological samples from an individual. Generally, these abnormal macrophages are present without identifiable concomitant T cell activation in the ALS patients.

As used herein, detecting the "presence of abnormal macrophages" generally means detecting the level of abnormal macrophages. Generally, the level of abnormal macrophages (or activated monocytes) is indicated by the level of HLA-DR expression in a population of CD14+ cells and/or the percentage of CD16+ cells in a population of CD14+ cells and/or the number of CD14+/CD16+ cells, although other markers that indicate monocyte activation, differentiation and/or proliferation could be used. It is understood that an absolute or even relative level need not be determined; an observation of detectable abnormal macrophages is sufficient.

A "proliferating macrophage" or "promac" is understood in the art and as used herein denotes a disease-associated blood macrophage which exhibits an elevation in proliferation and/or activation markers relative to non-disease blood macrophages. Normally a macrophage is a terminally differentiated cell incapable of further division. For purposes of this invention, a "proliferating macrophage" is capable of further division or is in a portion of the cell cycle not considered to be terminal or end stage, and/or has undergone inappropriate activation (e.g., are "inappropriately activated") or is undergoing inappropriate activation. Methods of detecting proliferating macrophage(s) are discussed below.

"Pathologic macrophages" as used herein is meant to encompass both proliferating macrophages and inappropriately activated macrophages (e.g., abnormal macrophages). Pathologic macrophages thus encompass proliferating macrophages, as defined above, as well as macrophages in the blood that may not exhibit proliferation markers at any given time, but are nonetheless chronically activated, and thus are in a pathogenic state.

As used herein, detecting the "presence of proliferating macrophages" generally means detecting the level of proliferating macrophages. It is understood that an absolute or even relative level need not be determined; an observation of detectable proliferating macrophages is sufficient.

A "macrophage-associated" disease, disorder or indication is a disease, disorder or indication that is associated with pathologic macrophages an elevated, or abnormal, level or rate of macrophage proliferation as compared to control sample(s). Such disorders include, but are not limited to, macrophage-associated neurodegenerative disorders, such as ALS, MS, HIV-associated neurological disorders, and AD. The terms "disorder" and "disease" are used interchangeably herein. An "HIV-associated" disease is defined more broadly as generally associated with or secondary to an HIV infection; "HIV-mediated" diseases, for example, are included in those considered to be "HIV-associated." In particular embodiments, the disorder contemplated for treatment according to the invention is not cancer (e.g., is a disease or disorder other than cancer). In other particular embodiments, the disorder contemplated for treatment according to the invention is not an autoimmune disease (e.g., the macrophage-associated is a disease or disorder other than an autoimmune disorder or disease). For example, the disorder is not graft rejection (transplant rejection). In other embodiments, the disorder treated is a viral infection, particularly an HIV or HCV infection (i.e., the patient is not virally infected, e.g., is not HIV-infected or HCV-infected) In still other embodiments, the disorder is not have HIV-associated dementia (e.g., the patient does not have AIDS dementia), "Macrophage-associated neurodegenerative disorder" is specifically defined herein to exclude cancer, HIV infection, HCV infection, and autoimmune diseases.

A "macrophage-associated neurodegenerative disorder" is a neurodegenerative disease in which the patient has pathologic macrophages (e.g., abnormally activated macrophages and/or proliferating macrophages, particularly a disease associated with an elevated, or abnormal, level or rate of macrophage proliferation as compared to control sample(s)). "Macrophage-associated neurodegenerative disorder" is specifically defined herein to exclude cancer and autoimmune diseases.

"Amyotrophic lateral sclerosis" or "ALS" are terms understood in the art and as used herein to denote a progressive neurodegenerative disease that affects upper motor neurons (motor neurons in the brain) and/or lower motor neurons (motor neurons in the spinal cord) and results in motor neuron death. As used herein, the term "ALS" includes all of the classifications of ALS known in the art, including, but not limited to classical ALS (typically affecting both lower and upper motor neurons), Primary Lateral Sclerosis (PLS, typically affecting only the upper motor neurons), Progressive Bulbar Palsy (PBP or Bulbar Onset, a version of ALS that typically begins with difficulties swallowing, chewing and speaking), Progressive Muscular Atrophy (PMA, typically affecting only the lower motor neurons) and familial ALS (a genetic version of ALS).

"Multiple sclerosis" or "MS" are terms understood in the art and as used herein to denote a progressive neurodegenerative disease resulting in destruction of the myelin covering of nerve cells, particularly of the brain and spinal cord. As used herein, "MS" includes all of the classifications of MS known in the art, including, but not limited Relapsing-remitting (RRMS) (typically characterized by partial or total recovery after attacks (also called exacerbations, relapses, or flares)), Secondary progressive (SPMS) (generally characterized by fewer relapses, with an increase in disability and symptoms), and Primary progressive (PPMS) (generally characterized by progression of symptoms and disability without remission).

"Alzheimer's disease" or "AD" are terms understood in the art and used herein to denote a progressive neurodegenerative disease characterized by dementia and defined by the American Psychiatric Association (in DSM IV) as the development of multiple cognitive deficits that includes memory impairment.

An "individual" is a vertebrate, preferably a mammal, more preferably a human. Mammals include, but are not limited to, farm animals, sport animals, rodents, primates, and pets.

A "macrophage-associated neurodegenerative disease individual" or a "macrophage-associated neurodegenerative disease patient" is an individual who is diagnosed as having a neurodegenerative disease or is suspected of having a neurodegenerative disease by demonstrating clinical symptoms of a neurodegenerative disease, which symptoms include pathologic macrophages in the patient's blood. A "non-macrophage-associated neurodegenerative disease individual" is an individual who is not diagnosed as having, and not suspected of having, a macrophage-associated neurodegenerative disease. "Macrophage-associated neurodegenerative disorder" is specifically defined herein to exclude cancer and autoimmune diseases.

An "ALS individual" or an "ALS patient" is an individual who is diagnosed as having ALS or is suspected of having ALS by demonstrating ALS-associated symptoms. A "non-ALS individual" is an individual who is not diagnosed as having ALS or not suspected of having ALS. ALS and methods of diagnosing ALS are known in the art and are discussed herein.

An "AD individual" or an "AD patient" is an individual who is diagnosed as having AD or is suspected of having AD by demonstrating AD-associated symptoms. A "non-AD individual" is an individual who is not diagnosed as having AD or not suspected of having AD. AD and methods of diagnosing AD are known in the art and are discussed herein.

An "MS individual" or an "MS patient" is an individual who is diagnosed as having MS or is suspected of having MS by demonstrating MS-associated symptoms. A "non-MS individual" is an individual who is not diagnosed as having MS or not suspected of having MS. MS and methods of diagnosing MS are known in the art and are discussed herein.

"Development" or "progression" of a disease, e.g., a macrophage-associated neurodegenerative disease such as ALS, of AD, or of MS, herein means initial manifestations and/or ensuing progression of the disorder. For example, development of ALS or of MS can be detectable and assessed using standard clinical techniques, such as nerve and muscle biopsy and CNS scanning technologies such as MRI. However, development also refers to disease progression that may be undetectable. For purposes of this invention, development or progression refers to the biological course of the disease state. "Development" includes occurrence, recurrence, and onset. As used herein "onset" or "occurrence" of ALS, AD, or MS includes initial onset and/or recurrence.

As used herein, "delaying development" of a macrophage-associated neurodegenerative disease a disease, such as ALS, AD or MS, means to defer, hinder, slow, retard, stabilize, and/or postpone development of one or more symptoms, of the disease, including decreasing the rate at which the patient's disease progresses (e.g., to shift the patient from rapidly progressing disease to a more slowly progressing disease). This delay can be of varying lengths of time, depending on the history of the disorder and/or the medical profile of the individual being treated. As is evident to one skilled in the art, a sufficient or significant delay can, in effect, encompass prevention, in that the individual does not develop detectable disease. A method that "delays" development of disease is a method that reduces the extent of the disease in a given time frame, when compared to not using the method. Such comparisons are typically based on clinical studies, using a statistically significant number of subjects, although this knowledge can be based upon anecdotal evidence. "Delaying development" can mean that the extent and/or undesirable clinical manifestations are lessened and/or time course of the progression is slowed or lengthened, as compared to not administering the agent. Thus the term also includes, but is not limited to, alleviation of symptoms, diminishment of extent of disease, stabilized (i.e., not worsening) state of disease, delay or slowing of disease progression, and remission (whether partial or total) whether detectable or undetectable.

As used herein, "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides. The term "biological sample" encompasses a clinical sample, and also includes cells in culture, cell supernatants, cell lysates, serum, plasma, biological fluid, and tissue samples. Generally, the sample will be, or be derived from, peripheral blood and as such is a "blood sample". In some cases, the blood will have been enriched for a macrophage fraction, by using, for example, glass or plastic adherence.

A "blood sample" is a biological sample which is derived from blood, preferably peripheral (or circulating) blood. A blood sample may be, for example, whole blood, plasma or serum.

As used herein, an "effective amount" (e.g., of an agent) is an amount (of the agent) that produces a desired and/or beneficial result. An effective amount can be administered in one or more administrations. In general, an effective amount is an amount sufficient to decrease the level of abnormal macrophages (pathologic macrophages) in a macrophage-associated neurodegenerative disease patient or derived from a macrophage-associated neurodegenerative disease individual. In some embodiments, an effective amount is an amount sufficient to decrease the level of abnormal macrophages in an ALS patient or derived from an ALS individual. In other embodiments, an effective amount is an amount sufficient to decrease the level of abnormal macrophages in an MS patient or derived from an MS individual. In other embodiments, an effective amount is an amount sufficient to decrease the level of abnormal macrophages in an AD patient or derived from an AD individual. An "amount sufficient to decrease the level of abnormal macrophages" preferably is able to decrease the level of abnormal macrophages by at least about 25%, preferably at least about 50%, more preferably at least about 75%, and even more preferably at least about 90%. Such a decrease may have desirable concomitant effects, such as to palliate, ameliorate, stabilize, reverse, slow or delay progression of disease, delay and/or even prevent onset of disease.

In other embodiments, "amount sufficient to decrease the level of HLA-DR expression by CD14+ cells" preferably is able to decrease the level of HLA-DR expression by at least about 25%, preferably at least about 50%, more preferably at least about 75%, and even more preferably at least about 90%. Such a decrease may have desirable concomitant effects, such as to palliate, ameliorate, stabilize, reverse, slow or delay progression of disease, delay and/or even prevent onset of disease.

As used herein, decreasing the "level of abnormal macrophages" generally means decreasing the population number of abnormal macrophages or activated monocytes and/or decreasing the level of HLA-DR expression in a population of CD14+ cells. In various embodiments, the level of abnormal macrophages can be assayed by determining the percentage of CD16+ cells in a population of CD14+ cells and/or the number of CD14+/CD16+ cells in the biological sample. It is understood that an absolute level need not be determined; an observation of a relative level of abnormal macrophages is sufficient.

"Modulating" macrophage proliferation means that the level or rate of proliferation is altered when compared to not administering an agent that changes macrophage proliferation. For example, "modulating" macrophage proliferation through use of chlorite-containing composition means that the level of proliferating macrophages or the rate of proliferation is altered when compared to not administering the agent. Preferably, "modulating" macrophage proliferation means a change in the level of proliferating macrophages or the rate of macrophage proliferation of at least 25%, preferably at least 50%, more preferably at least 75%, and even more preferably at least 90%. Generally, for purposes of this invention, "modulating" macrophage proliferation means that the level of proliferating macrophages or the rate of proliferation is decreased when compared to the same parameter in that individual when no agent is administered. However, during the course of therapy, for example, it may be desirable to increase the level of proliferating macrophages or the rate of proliferation from a previously measured level. The degree of modulation may be assessed by measurement of macrophage proliferation, which will be discussed below, and generally entails detecting a proliferation marker(s) in a macrophage population or uptake of certain substances such as BrdU or 3H-thymidine (which would provide a quantitative measure of proliferation). Further, it is possible that, if the macrophages are proliferating due to a genetic alteration (such as transposition, deletion, or insertion), this alteration could be detected using standard techniques in the art, such as RFLP (restriction fragment length polymorphism).

"Treatment" or "treating" as used herein means any therapeutic intervention in a subject, usually a mammalian subject, generally a human subject, including: (i) prevention, that is, causing overt clinical symptoms not to develop, e.g., preventing disease progression to a harmful state; (ii) inhibition, that is, arresting the development or further development of clinical symptoms, e.g., mitigating existing clinical symptoms; and/or (iii) relief, that is, causing the regression of clinical symptoms, e.g., causing relief from clinical symptoms.

Exemplary clinical symptoms of ALS include muscle weakness, muscle wasting, muscle cramping, muscle twitching, slurred or slow speech, difficulty swallowing, and slow, uncoordinated movements. Further exemplary clinical symptoms of ALS include those detectable in a biological sample obtained from a subject having or suspected of having ALS, e.g., increased CD4:CD8 cell ratio compared to normal, decreased number of CD14+ cells compared to normal, increased expression of HLA-DR on CD14+ cells compared to normal CD14+ cells, increased levels of activated monocytes or macrophages compared to normal, the presence of proliferating macrophages, and decreased serum IgG and/or IgM compared to normal, where "normal" as used herein means a subject unaffected by ALS or cells from such an unaffected subject. "Treating" thus encompasses achieving a decrease in one or more clinical symptoms, which decrease may have desirable concomitant effects, such as to palliate, ameliorate, stabilize, reverse, slow or delay progression of disease, delay and/or even prevent onset of disease.

Exemplary clinical symptoms of AD include mild forgetfulness, including trouble remembering recent events, activities, or the names of familiar people or things; difficulty in solving simple math problems; trouble remembering how to do simple tasks (e.g., brushing teeth or combing hair); inability to think clearly; difficulty speaking, understanding, reading, or writing; and anxiety or aggressiveness, or tendency to wander away from home.

Exemplary clinical symptoms of MS include fatigue (also referred to as MS lassitude), muscle fatigue, paresthesias, difficulty in walking and/or balance problems, abnormal sensations such as numbness, prickling, or "pins and needles", pain, bladder dysfunction, bowel dysfunction, changes in cognitive function (including problems with memory, attention, concentration, judgment, and problem-solving), dizziness and vertigo, emotional problems (e.g., depression), sexual dysfunction, and vision problems. Severe cases can involve partial or complete paralysis. (such as blurred or double vision, red-green color distortion, or even blindness in one eye). Other symptoms include headache, hearing loss, itching, seizures, spasticity, speech and swallowing disorders, and tremors. Further exemplary clinical symptoms of MS include those detectable in a biological sample obtained from a subject having or suspected of having MS, e.g., increased CD4:CD8 cell ratio compared to normal, decreased number of CD14+ cells compared to normal, increased expression of HLA-DR on CD14+ cells compared to normal CD14+ cells, increased levels of activated monocytes or macrophages compared to normal, the presence of proliferating macrophages, and decreased serum IgG and/or IgM compared to normal, where "normal" as used herein means a subject unaffected by MS or cells from such an unaffected subject. "Treating" thus encompasses achieving a decrease in one or more clinical symptoms, which decrease may have desirable concomitant effects, such as to palliate, ameliorate, stabilize, reverse, slow or delay progression of disease, delay and/or even prevent onset of disease.

The terms "subject" and "patient" mean a member or members of any mammalian or non-mammalian species that may have a need for the pharmaceutical methods, compositions and treatments described herein. Subjects and patients thus include, without limitation, primate (including humans), canine, feline, ungulate (e.g., equine, bovine, swine (e.g., pig)), avian, and other subjects. Humans and non-human animals having commercial importance (e.g., livestock and domesticated animals) are of particular interest.

"Mammal" means a member or members of any mammalian species, and includes, by way of example, canines; felines; equines; bovines; ovines; rodentia, etc. and primates, particularly humans. Non-human animal models, particularly mammals, e.g. primate, murine, lagomorpha, etc. may be used for experimental investigations.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable excipient (e.g., pharmaceutically acceptable diluent, carrier or vehicle).

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. "A pharmaceutically acceptable excipient" as used in the specification and claims includes both one and more than one such excipient.

Chlorite and Administration Thereof

The source of chlorite ions for administration of chlorite according to the invention can be provided in a variety of forms. For example, chlorite can be administered as a chlorite salt (e.g., alkali metal salt, e.g., sodium chloride, potassium chlorite, and the like) or a mixture of chlorite salts, where the chlorite salts are preferably pharmaceutically acceptable. In addition or alternatively, chlorite can be administered as a matrix of chlorite ions, e.g., described in U.S. Pat. No. 4,507,285. In one embodiment, the chlorite ions are provided in a compositions having the general formula $$ClO_2 \times nO_2$$

wherein "n" can be a value of about 0.1-0.25. Such agents can have an $O_2$ band at 1562 cm$^{-1}$ in the Raman spectrum and an O-O interval of 123 pm. Production of such agents is known in the art, see, e.g., U.S. Pat. No. 4,507,285.

In one embodiment, the method of treatment involves administration of an aqueous solution of a product known as "tetrachlorodecaoxygen anion complex", commonly abbreviated as "TCDO". Production of TCDO is well known, see, e.g., Example 1 of U.S. Pat. No. 4,507,285.

As appropriate, agents that provide a source of chlorite ions can be administered in a free base or free acid form (that is, as the free compound and not as a salt). Additionally, any pharmaceutically acceptable salt(s) of the compound(s) can also be used. Pharmaceutically acceptable salts are those salts which retain the biological activity of the free compounds and which are not biologically or otherwise undesirable. As appropriate, stereoisomers of the compounds disclosed can also be used in the invention, including diastereomers and enantiomers, as well as mixtures of stereoisomers, including, but not limited to, racemic mixtures. Unless stereochemistry is explicitly indicated in a structure, the structure is intended to embrace all possible stereoisomers of the compound depicted.

Formulations

Chlorite can be provided in any suitable formulation, which can be selected according to the desired route of administration.

U.S. Pat. No. 4,725,437 describes an aqueous solution of a chemically stabilized chlorite matrix suitable for intravenous administration in a dosed amount of about $6.2\times10^{-6}$ mole of $ClO_2^{--}$ to $9.3\times10^{-5}$ mole of $ClO_2^{--}$ per kg of body weight in humans and non-human animals. The solution contains the chlorite matrix in a concentration of about 12 to 72 micromol of $ClO_2^{--}$ per ml. Further chlorite formulations are described in U.S. Pat. Nos. 4,507,285 and 4,725,437.

Formulations of TCDO are of particular interest in the present invention. WF10 is a TCDO formulation of particular interest in the practice of the invention. WF10, also known as Oxoferin (Oxo Chemie GmbH, Fort Worth, Tex.), is available commercially. Other formulations of TCDO are within the scope of this invention.

Chlorite-containing compositions, such as TCDO, can be formulated for parenteral or enteral administration, generally parenteral administration. Accordingly, formulations of chlorite are suitable for parenteral, topical, or transdermal administration, usually intravenous, intramuscular, or subcutaneous administration, and may be suitable for administration by bolus injection, sustained release (including controlled release), infusion, and the like. Administration by infusion (e.g., by subcutaneous or intravenous infusion) is of interest, as is administration in the form of suppositories. Additional agents and therapies Chlorite can be administered alone or in various combinations. Where administered in combination, chlorite can be administered in conjunction with other agents, particularly those suitable for protective, palliative or supportive care of the subject. The phrase "in conjunction with" means that an agent is administered prior to, concurrently, or after other substance or therapy. Examples of agents for administration in conjunction with an agent include, but are not limited to, riluzole. Other agents for administration in conjunction with chlorite include agents for control of symptoms of a macrophage-associated neurodegenerative disorder, such as ALS, AD or MS symptoms. Further exemplary agents for administration in conjunction with chlorite according to the invention include, but are not limited to, baclofen, diazepam, trihexyphenidyl and/or amitriptyline. Chlorite can also be administered in conjunction with non-drug therapy (e.g., physical and/or occupational therapy, massage, and the like).

In one embodiment, the composition does not contain an amount of another anti-proliferative agent, such as a polyamine analog, effective to decrease the level of abnormal macrophages in a macrophage-associated neurodegenerative disorder patient, such as an ALS, AD, or MS patient (e.g., as compared to prior to therapy). For example, TCDO has been described for administration in combination therapy with anti-proliferative agents where TCDO is administered in an amount effective to promote macrophage phagocytosis to facilitate delivery of the anti-proliferative agent to the macrophage. The present invention contemplates that chlorite ions (e.g., as a pharmaceutically acceptable salt or in a stabilized matrix, such as in TCDO) are administered to a macrophage-associated neurodegenerative disorder patient, such as an ALS, AD or MS patient so that the chlorite is the active ingredient present in the subject in an amount effective to facilitate treatment of the patient e.g., through reduction in proliferating/inappropriately activated macrophages, and without the need for administration of for example, a polyamine analog or other anti-proliferative agent in conjunction with chlorite.

Administration and Dosing

Chlorite formulations are generally dosed in vivo corresponding to the body weight of the subject. Due to the continuous breakdown of the active agent in the blood, the agent is normally administered at regular intervals. Those of skill in the art will readily appreciate that actual dosages and regimen will vary as a function of the agent, formulation, the severity of the symptoms, the susceptibility of the subject to treatment and/or side effects, and the like. Dosages are readily and routinely determinable by those of skill in the art by a variety of means.

Exemplary doses of chlorite-containing formulations can vary between about 0.1 ml/kg to about 1.5 ml/kg, preferably, about 0.5 ml/kg of body weight and at a concentration of about 40 to about 80 mMol $ClO_2^-$ per liter, usually about 60 mMol $ClO_2^-$ per liter, respectively. In the case of TCDO, a dose finding phase I/II study evaluating WF-10 administered intravenously and involving 48 patients established a maximum dose of approximately 0.5 ml/kg. Other suitable doses may be approximately 0.25 ml/kg.

The regimen of administration (e.g., dose combined with frequency of administration) will generally involve administration in an amount and at a frequency to provide for a desired effect, e.g., administration of an amount effective to provide for improvement in one or more symptoms of a macrophage-associated neurodegenerative disorder patient, such as one or more ALS, AD or MS symptoms. For example, chlorite can be administered for 2, 3, 4, 5, 6, 7, 8, 9, 10 or more consecutive days, which administration period may be reinitiated after 1, 2, 3 or more weeks following the last dose. In one exemplary embodiment, a WF-10 regimen comprises 5 consecutive days of treatment every 3 weeks.

In one embodiment, chlorite is administered so as to effect modulation of macrophage proliferation, e.g., alteration of the level of proliferating macrophages or the rate of macrophage proliferation compared to in the absence of agent administration, and/or to effect modulation of inappropriate macrophage activation. An effective amount of chlorite is determined by, for example, comparing the level (or number) of promacs, before and during treatment, with a downward trend in the number of promacs generally being consistent with a positive effect. In one embodiment, chlorite is administered so as to effect a change in the level of proliferating macrophages or the rate of macrophage proliferation of at least 25%, preferably at least 50%, more preferably at least 75%, and even more preferably at least 90%. The degree of modulation may be assessed by measurement of macrophage proliferation as described in the art, and generally entails detecting a proliferation marker(s) in a macrophage population or uptake of certain substances such as BrdU or 3H-thymidine (which would provide a quantitative measure of proliferation) (see, e.g., U.S. Publication No. 20030175832). Such a decrease may have desirable concomitant effects, such as to palliate, ameliorate, stabilize, reverse, slow and/or delay progression of disease, delay or even prevent onset of disease.

Methods for detecting proliferating or inappropriately activated macrophages and determining macrophage proliferation rates are known in the art. For example, proliferating macrophages may be detected by assaying cell proliferative markers, such as PCNA, Ki67 or uptake of bromodeoxyuridine (BrdU) or 3H-thymidine. These markers are distinct from those that identify only "activated" macrophages (as opposed to proliferating macrophages), such as CD69 and CD25. The cellular subset representing macrophages may in turn be identified by detection of certain cell specific markers, such as CD14, CD68, CD16, or nonspecific esterase. Detection of these cell-type and/or proliferative markers use methods standard in the art, such as staining techniques and FACS sorting and analysis.

In another embodiment, chlorite is administered to as to effect a decrease in the level (e.g., number) of pathologic macrophages, e.g., to effect a decrease in the level of CD14+ monocytes, preferably activated CD14+ monocytes, in a patient with a macrophage-associated neurodegenerative disorder (e.g., a patient with ALS, with AD, or with MS). In this embodiment, chlorite is administered in an amount sufficient to decrease the level of (e.g., number of) CD14+ monocytes, preferably activated CD14+ monocytes and/or CD14+ monocytes with elevated HLA-DR expression and/or the number of CD14+/CD16+ cells and/or the percentage of CD16+ cells in a population of CD14+ cells in the individual (i.e., an effective amount). An effective amount of chlorite is determined by, for example, comparing the level of number of CD14+ monocytes, preferably activated CD14+ monocytes, before and during treatment, with a downward trend of number of CD14+ monocytes generally being consistent with a positive effect. An "amount sufficient to decrease the number of CD14+ monocytes" preferably is able to decrease the number of CD14+ monocytes by at least about 25%, preferably at least about 50%, more preferably at least about 75%, and even more preferably at least about 90%. Methods for assessing levels of CD14+ monocytes, activated CD14+ monocytes, CD14+ monocytes with elevated HLA-DR expression, CD14+/CD16+ cells and the percentage of CD16+ cells in a population of CCD14+ are known in the art (see, e.g., U.S. Publication No. 20030175832). Such a decrease may have desirable concomitant effects, such as to palliate, ameliorate, stabilize, reverse, slow and/or delay progression of disease, delay or even prevent onset of disease.

Levels of pathologic macrophages (proliferating/inappropriate activated macrophages (promacs)), macrophage proliferation rate, CD14+ cells, HLA-DR expression, and the like as set out above can be compared to a level from the same individual measured at a different time and/or under different conditions (such as before treatment, different dose, etc.), and/or to a mean or median level determined for a non-diseased standard (e.g., non-macrophage-associated neurodegenerative disorder patient, such as a non-ALS, non-AD, or non-MS, as appropriate), for example from an unaffected individual (e.g., non-macrophage-associated neurodegenerative disorder individual or individuals; a non-ALS individual or non-ALS individuals; or non-AD individual or non-AD individuals; or non-MS individual or non-MS individuals).

For example, an HLA-DR expression level may be compared to an HLA-DR level from the same individual measured at a different time and/or under different conditions (such as before treatment, different dose, etc.). In some embodiments, an HLA-DR expression level is compared to a mean or median level of HLA-DR expression determined on a population of CD14+ cells from a non-diseased (e.g., non-ALS, non-AD, or non-MS) standard, for example from a non-ALS individual or non-ALS individuals, or non-MS individual or non-MS individuals, or non-AD individual or non-AD individuals). A finding of HLA-DR expression level of greater than about 1.4 fold that of the non-diseased standard is indicative of an elevated level of HLA-DR expression in the individual. Generally, a finding of HLA-DR expression level of greater than about 1.5 fold, greater than about 1.6 fold, greater than about 1.7 fold, greater than about 1.8 fold, greater than about 1.9 fold, greater than about 2.0 fold, greater than about 5.0 fold, or greater than about 10 fold that of a non-diseased standard is indicative of an elevated level of HLA-DR expression in the individual. Thus, decreasing HLA-DR expression in a macrophage-associated neurodegenerative disorder subject (e.g., an ALS subject, an AD subject, or an MS subject) so as to more closely approximate an HLA-DR expression level in a non-diseased subject (e.g., non-ALS, non-AD, or non-MS subject) is of interest in the present invention.

In another example, the number of CD14+/CD16+ cells or the percentage of CD16+ cells in a population of CD14+ cells in a sample from a macrophage-associated neurodegenerative disorder subject (e.g., an ALS subject, an AD subject, or an MS subject) is compared to a mean or median level of CD14+/CD16+ cells in a biological sample from a non-disease (e.g., non-ALS, non-AD, or non-MS) standard, for example from a non-ALS individual or non-ALS individuals; or non-AD individual or non-AD individuals or non-MS individual or non-MS individuals. A finding of a percentage of CD16+ cells in a population of CD14+ cells and/or the number of CD14+/CD16+ cells in a sample of greater than about 1.5 fold, greater than about 1.6 fold, greater than about 1.7 fold, greater than about 1.8 fold, greater than about 1.9 fold, greater than about 2.0 fold, greater than about 3.0 fold, greater than about 4.0 fold, greater than about 5.0 fold, or greater than about 10 fold that of a non-diseased (non-ALS, non-AD, or non-MS) standard is indicative of an increased number of CD14+/CD16+ cells in the individual. Thus, in one embodiment, therapy according to the invention is provided so as to decrease the number of CD14+/CD16+ cells or the percentage of CD16+ cells in a population of CD14+ cells so as to more closely approximate such in an appropriate non-diseased subject.

In general, therapy is monitored by following blood macrophage activation, usually by following CD14/DR levels and the percentage of CD14/16 positive cells as described above.

Kits with unit doses of the subject compounds, usually in injectable doses, are provided. In such kits, in addition to the containers containing the unit doses will be an informational package insert describing the use and attendant benefits of chlorite in treating a macrophage-associated neurodegenerative disorder subject, such as ALS, AD, or MS. Preferred compounds and unit doses are those described herein above.

Subjects and Monitoring Therapy

In general, individuals suitable for therapy involving administration of chlorite according to the invention include individuals who have been diagnosed as having a macrophage-associated neurodegenerative disorder, are "afflicted with" a macrophage-associated neurodegenerative disorder (e.g., diagnosed as having, suffering from and/or displaying one or more clinical symptoms), or who have been adjudged to be at high risk for developing such a disorder. An "at risk" or "high risk" individual is an individual who has a discrete and significant risk of developing a macrophage-associated neurodegenerative disorder. An "at risk" or "high risk" individual may or may not have detectable disease, and may or may not have displayed detectable disease prior to receiving the method(s) described herein. "High risk" (or "at risk") denotes that an individual has one or more so-called risk factors, which are measurable parameters that correlate with development of disease. An individual having one or more of these risk factors has a higher probability of developing disease than an individual without these risk factor(s). These risk factors include, but are not limited to, genetic (i.e., hereditary) considerations (including family history and genetic markers). It is understood that having only one risk factor can often indicate high risk. The clinician, as one skilled in the art, has discretion to determine whether treatment using an agent may be indicated for an individual at risk. Exemplary a macrophage-associated neurodegenerative disorders includes ALS, AD, and MS.

In one embodiment, individuals suitable for therapy involving administration of chlorite according to the invention include individuals who have been diagnosed as having ALS, are "afflicted with" ALS (e.g., diagnosed as having, suffering from and/or displaying one or more clinical symptoms of) ALS, or who have been adjudged to be at high risk for developing such a disorder. An "at risk" or "high risk" individual is an individual who has a discrete and significant risk of developing ALS. An "at risk" or "high risk" individual may or may not have detectable disease, and may or may not have displayed detectable disease prior to receiving the method(s) described herein. "High risk" (or "at risk") denotes that an individual has one or more so-called risk factors, which are measurable parameters that correlate with development of disease. An individual having one or more of these risk factors has a higher probability of developing disease than an individual without these risk factor(s). These risk factors include, but are not limited to, genetic (i.e., hereditary) considerations (including family history and genetic markers). It is understood that having only one risk factor can often indicate high risk. The clinician, as one skilled in the art, has discretion to determine whether treatment using an agent may be indicated for an individual at risk.

Exemplary clinical symptoms of ALS include muscle weakness, muscle wasting, muscle cramping, muscle twitching, slurred or slow speech, difficulty swallowing, and slow, uncoordinated movements. Further exemplary clinical symptoms of ALS include those detectable in a biological sample obtained from a subject having or suspected of having ALS, e.g., increased CD4:CD8 cell ratio compared to normal, decreased number of CD14+ cells compared to normal, increased expression of HLA-DR on CD14+ cells compared to normal CD14+ cells, increased levels of activated monocytes or macrophages compared to normal, the presence of proliferating macrophages, and decreased serum IgG and/or IgM compared to normal, where "normal" as used herein means a subject unaffected by ALS or cells from such an unaffected subject.

In another embodiment, individuals suitable for therapy involving administration of chlorite according to the invention include individuals who have been diagnosed as having MS, are "afflicted with" MS (e.g., diagnosed as having, suffering from and/or displaying one or more clinical symptoms of) MS, or who have been adjudged to be at high risk for developing such a disorder. An "at risk" or "high risk" individual is an individual who has a discrete and significant risk of developing MS. An "at risk" or "high risk" individual may or may not have detectable disease, and may or may not have displayed detectable disease prior to receiving the method(s) described herein. "High risk" (or "at risk") denotes that an individual has one or more so-called risk factors, which are measurable parameters that correlate with development of disease. An individual having one or more of these risk factors has a higher probability of developing disease than an individual without these risk factor(s). These risk factors include, but are not limited to, genetic (i.e., hereditary) considerations (including family history and genetic markers). It is understood that having only one risk factor can often indicate high risk. The clinician, as one skilled in the art, has discretion to determine whether treatment using an agent may be indicated for an individual at risk.

Exemplary clinical symptoms of MS include those detectable in a biological sample obtained from a subject having or suspected of having MS, e.g., increased CD4:CD8 cell ratio compared to normal, decreased number of CD14+ cells compared to normal, increased expression of HLA-DR on CD14+ cells compared to normal CD14+ cells, increased levels of activated monocytes or macrophages compared to normal, the presence of proliferating macrophages, and decreased serum IgG and/or IgM compared to normal, where "normal" as used herein means a subject unaffected by MS or cells from such an unaffected subject.

In another embodiment, individuals suitable for therapy involving administration of chlorite according to the invention include individuals who have been diagnosed as having AD, are "afflicted with" AD (e.g., diagnosed as having, suffering from and/or displaying one or more clinical symptoms of) AD, or who have been adjudged to be at high risk for developing such a disorder. An "at risk" or "high risk" individual is an individual who has a discrete and significant risk of developing AD. An "at risk" or "high risk" individual may or may not have detectable disease, and may or may not have displayed detectable disease prior to receiving the method(s) described herein. "High risk" (or "at risk") denotes that an individual has one or more so-called risk factors, which are measurable parameters that correlate with development of disease. An individual having one or more of these risk factors has a higher probability of developing disease than an individual without these risk factor(s). These risk factors include, but are not limited to, genetic (i.e., hereditary) considerations (including family history and genetic markers). It is understood that having only one risk factor can often indicate high risk. The clinician, as one skilled in the art, has discretion to determine whether treatment using an agent may be indicated for an individual at risk.

Exemplary clinical symptoms of AD include mild forgetfulness, including trouble remembering recent events, activities, or the names of familiar people or things; difficulty in solving simple math problems; trouble remembering how to do simple tasks (e.g., brushing teeth or combing hair); inability to think clearly; difficulty speaking, understanding, reading, or writing; and anxiety or aggressiveness, or tendency to wander away from home. Further exemplary clinical symptoms of AD include those detectable in a biological sample obtained from a subject having or suspected of having AD, e.g., increased CD4:CD8 cell ratio compared to normal, decreased number of CD14+ cells compared to normal, increased expression of HLA-DR on CD14+ cells compared to normal CD14+ cells, increased levels of activated monocytes or macrophages compared to normal, the presence of proliferating macrophages, and decreased serum IgG and/or IgM compared to normal, where "normal" as used herein means a subject unaffected by AD or cells from such an unaffected subject.

Monitoring Therapy

Chlorite-based therapy according to the invention can be monitored, and dosages and regimen adjusted accordingly, by assessing the effect of therapy upon one or more clinical symptoms. In general, an effective amount of chlorite is a dose or doses that provide for an improvement in one or more clinical symptoms in the subject.

For example, since elevated HLA-DR expression on CD14+ cells and/or increased numbers of CD14+/CD16+ cells and/or the percentage of CD16+ cells in a population of CD14+ cells is associated with a macrophage-associated neurodegenerative disorder (e.g., ALS, AD, MS), monitoring these levels can be used to facilitates assessment of initial responsiveness to therapy and/or efficacy, as well as the appropriate dosage of the therapy. Similarly, since elevated HLA-DR expression on CD14+ cells and/or increased numbers of CD14+/CD16+ cells and/or the percentage of CD16+ cells in a population of CD14+ cells is associated with MS, monitoring these levels can be used to facilitates assessment of initial responsiveness to therapy and/or efficacy, as well as the appropriate dosage of the therapy.

It is understood that monitoring therapy means that symptoms are assessed at different times and are compared over time. Where assessment of a clinical symptom requires analysis of a biological sample, such biological sample(s) are generally obtained at different times, for example, during application of therapy, and are compared, either with each other, a control, and/or a desired value. Methods for monitoring ALS therapy through assessment of biological samples is described in, for example, U.S. Publication No. 20030175832.

For example, therapy for a macrophage-associated neurodegenerative disorder, such as ALS, AD or MS therapy can be monitored by determining the level of HLA-DR expression by CD14+ cells from peripheral blood. In another embodiment, monitoring therapy includes the step of determining the level of CD14+ cells expressing elevated HLA-DR in a blood sample, preferably peripheral blood. In another embodiment, monitoring therapy includes the step of determining the percentage of CD16+ cells in the population of CD14+ cells in a blood sample, preferably peripheral blood. In another embodiment, monitoring therapy includes the step of determining the number of CD14+/CD16+ cells in a blood sample, preferably peripheral blood. In another embodiment, the level of abnormal macrophages (in various embodiments, the level of CD14+ cells expressing elevated HLA-DR; the percentage of CD16+ cells in the population of CD14+ cells and/or the number of CD14+/CD16+ cells) in a blood sample determined during and/or at completion of the therapy is generally compared with the level in a control sample and/or with a desired value. In another embodiment, monitoring therapy also includes the step of measuring proliferation of the abnormal macrophages.

In another embodiment, therapy for a macrophage-associated neurodegenerative disorder, such as ALS, AD or MS therapy is monitored by assessing the level of abnormal macrophages in a sample taken at a particular time from a patient undergoing the therapy and/or a sample taken after or at completion of the therapy is generally compared with the level in a sample taken from the patient prior to the therapy and/or with the level in a sample taken from the patient at a different time point in the therapy. For example, a decrease in the level of abnormal macrophages in the sample taken during therapy as compared to the sample taken prior to or at an earlier time point in therapy would generally be consistent with a positive effect of the therapy.

In another embodiment, therapy according to the invention is monitored by assessing the level of abnormal macrophages is assessed by the determining the level of HLA-DR expression by CD14+ cells from a blood sample, such as a peripheral blood sample. For example, the effect of a therapy is determined by comparing the level of HLA-DR expression by CD14+ cells in peripheral blood before and during treatment, with a downward trend in HLA-DR expression generally being consistent with a positive effect.

In another embodiment, therapy according to the invention is monitored by assessing the level of pathologic macrophages, e.g., by assessing the level of abnormal macrophages is assessed by the determining the percentage of CD16+ cells in the population of CD14+ cells from a blood sample, such as a peripheral blood sample. For example, the effect of a therapy is determined by comparing the percentage of CD16+ cells in the population of CD14+ cells in peripheral blood before and during treatment, with a downward trend in the percentage of CD14+/CD16+ cells generally being consistent with a positive effect.

In another embodiment, therapy according to the invention is monitored by assessing the level of pathologic macrophages, e.g., by assessing the level of abnormal macrophages is assessed by the determining the number of CD14+/CD16+ cells in a blood sample, such as a peripheral blood sample. For example, the effect of a therapy is determined by comparing the number of CD14+/CD16+ cells in peripheral blood before and during treatment, with a downward trend in the number of CD14+/CD16+ cells generally being consistent with a positive effect.

Kits

The invention also contemplates kits with unit doses of a source of chlorite ions, e.g., a chlorite salt (e.g., alkali metal salt, e.g., sodium chlorite, potassium chlorite, and the like); a mixture of chlorite salts; a matrix of chlorite ions, e.g., a compositions having the general formula $ClO_2 \times nO_2$, wherein "n" can be a value of about 0.1-0.25; e.g., TCDO. In general such unit doses are in injectable dosage forms, more particularly dosage forms suitable for infusion. In such kits, in addition to the containers containing the unit doses will be an informational package insert describing the use and attendant benefits of chlorite in treating a macrophage-associated neurodegenerative disorder subject, such as ALS, AD, or MS. Optionally, the kit includes information relating to identification of patients having a macrophage-associated neurodegenerative disease and monitoring of therapy of such patients (e.g., information relating to assessment of pathologic macrophages, e.g., proliferating macrophages, activated macrophages).

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Methods and Materials

The following methods and materials were used in the Examples set out below.

Subjects

Forty patients with ALS (mean age±SD, 59.5±13.3 yr), diagnosed by El Escorial criteria (Brooks et al. El Escorial World Federation of Neurology criteria for the diagnosis of amyotrophic lateral sclerosis. Subcommittee on Motor Neuron Diseases/Amyotrophic Lateral Sclerosis of the World Federation of Neurology Research Group on Neuromuscular Diseases and the El Escorial "Clinical limits of amyotrophic lateral sclerosis" workshop contributors. *J. Neurol. Sci.* 124 (suppl):96-107) at the Forbes Norris MDA/ALS Research Center (San Francisco, Calif., USA) had blood drawn in accordance with the CPMC and UCSF committees on human research guidelines, coordinated by the UCSF AIDS and Cancer Specimen Resource (ACSR) program. Revised ALS Functional Rating Scale (ALSFRS-R), scored 0-48, used to evaluate overall functional status in clinical trials as well as in clinical practice (Cedarbaum et al. 1999. The ALSFRS-R: a revised ALS functional rating scale that incorporates assessments of respiratory function. *J. Neurol. Sci.* 169:13-21), were used to evaluate each patient's clinical status and were updated within a month of blood testing.

The forty patients consisted of 26 men (age range, 34-87 yr; mean age±SD, 58.0±14.0 yr) and 14 women (age range, 40-77 yr; mean age±SD, 62.4±11.7 yr). They had had ALS for 4 to 93 months with a range of ALSFRS-R scores of 8 to 43.

Only two patients had familial ALS (fALS) and 38 patients were diagnosed with sporadic ALS (sALS). Demographic information on ALS patients (abbreviated in the table as "Pt") whose specimens were studied is shown in Table 1, in which thirteen of patients were using various anti-inflammatory medications with standard dose (Celebrex, Vioxx, Naproxyn, Excedrin), and 31 patients were taking riluzole (50 mg twice daily); ten patients received both medications.

on CD14 cells. CD16 (Fc gamma III receptor) expression on CD14 cells was used as another marker for monocyte differentiation and has been an antigen associated with cytokine expression patterns characteristic of tissue macrophages (Ziegler-Heitbrock et al. 1993. Eur. J. Immunol. 23:2053-2058; Frankenberger et al. 1996. Blood. 87:373-377). The monocyte granularity associated with its differentiation was measured by CD14-associated "backgating" on side light-

TABLE 1

Clinical summary

| Pt ID# | Pt Age (yrs) | Pt Sex | Disease Form | Therapy riluzole[A] | NSAIDS[B] | Duration of Illness (Months) | ALSFRS-R Score |
|---|---|---|---|---|---|---|---|
| Pt 1  | 76 | F | sALS | No  | No       | 46 | 19  |
| Pt 2  | 59 | M | sALS | Yes | No       | 15 | 30  |
| Pt 3  | 77 | F | sALS | Yes | No       | 37 | 34  |
| Pt 4  | 73 | F | fALS | Yes | No       | 31 | 20  |
| Pt 5  | 57 | M | sALS | Yes | Celebrex | 19 | 34  |
| Pt 6  | 63 | F | sLAS | Yes | Vioxx    | 10 | N/A |
| Pt 7  | 75 | F | sALS | No  | No       | 78 | 33  |
| Pt 8  | 64 | M | sALS | Yes | No       | 43 | 13  |
| Pt 9  | 58 | F | sLAS | Yes | No       | 42 | 28  |
| Pt 10 | 72 | M | sALS | Yes | No       | 18 | 26  |
| Pt 11 | 40 | F | sALS | Yes | No       | 12 | 28  |
| Pt 12 | 58 | M | sLAS | Yes | Celebrex | 21 | 18  |
| Pt 13 | 55 | M | sALS | Yes | No       | 85 | N/A |
| Pt 14 | 82 | M | sALS | No  | Celebrex | 4  | N/A |
| Pt 15 | 67 | M | sLAS | Yes | Celebrex | 45 | 20  |
| Pt 16 | 79 | M | sALS | Yes | No       | 14 | 15  |
| Pt 17 | 49 | M | sALS | No  | No       | 88 | 16  |
| Pt 18 | 60 | M | sLAS | No  | No       | 18 | 32  |
| Pt 19 | 49 | M | sALS | Yes | N/A      | 26 | 29  |
| Pt 20 | 37 | M | sALS | Yes | Celebrex | 82 | 8   |
| Pt 21 | 70 | M | sALS | Yes | No       | 29 | N/A |
| Pt 22 | 49 | M | sALS | Yes | No       | 14 | 39  |
| Pt 23 | 41 | F | sALS | Yes | No       | 33 | 37  |
| Pt 24 | 58 | M | sALS | Yes | No       | 20 | 32  |
| Pt 25 | 30 | M | sLAS | No  | No       | 24 | 35  |
| Pt 26 | 65 | M | sLAS | Yes | No       | 18 | 42  |
| Pt 27 | 41 | M | sALS | Yes | No       | 43 | 43  |
| Pt 28 | 58 | M | sALS | Yes | Celebrex | 25 | 26  |
| Pt 29 | 66 | F | sLAS | Yes | No       | 6  | 39  |
| Pt 30 | 63 | F | sALS | Yes | Excedrin | 18 | 34  |
| Pt 31 | 65 | M | sALS | Yes | Celebrex | 33 | 34  |
| Pt 32 | 52 | F | fALS | No  | Celebrex | 8  | 26  |
| Pt 33 | 34 | M | sALS | Yes | Celebrex | 41 | 15  |
| Pt 34 | 47 | M | sLAS | Yes | No       | 17 | 38  |
| Pt 35 | 62 | M | sALS | Yes | No       | 57 | 43  |
| Pt 36 | 87 | M | sALS | No  | No       | 93 | 25  |
| Pt 37 | 64 | F | sLAS | Yes | Celebrex | 45 | 35  |
| Pt 38 | 60 | F | sALS | Yes | No       | 27 | 23  |
| Pt 39 | 65 | F | sLAS | Yes | No       | 27 | 30  |
| Pt 40 | 53 | M | sALS | No  | Naproxyn | 45 | 37  |

[A]50 mg twice daily.
[B]Standard dose.

37 normal control blood samples (mean age±SD, 41.8±9.2 yr) were obtained from blood draws at Stanford University Blood Center and processed in a similar manner to the ALS patient blood specimens. They consisted of 21 men (age range, 25-61 yr; mean age±SD, 43.5±8.6 yr) and 16 women (age range, 25-59 yr; mean age±SD, 35.9±9.7 yr). Control samples for IgG and IgM studies consisted of plasma from 80 blood donors and were also obtained from the Stanford University Blood Center.

Flow Cytometry 10 ml of peripheral blood was drawn from each patient and normal controls into heparinized tubes and transferred to the laboratory at room temperature for same day immunologic studies. Cellular immunologic activation was evaluated by quantitating levels of CD38 on T-cell subsets and HLA-DR scatter characteristics (SSC). Whole blood was stained with CD14-fluorescein isothiocyanate (FITC), CD16-phycoerythrin (PE) (DAKO, Carpinteria, Calif., USA), CD8-FITC, CD38-PE, HLA-DR-PE, and CD4-peridinin chlorophyll protein (PerCP) (Becton-Dickinson, San Jose, Calif., USA) for 15 minutes at room temperature. Negative controls consisted of aliquots stained with isotype IgG-FITC, IgG-PE, and IgG-PerCP; all staining was performed as per manufacturers specifications. Samples were then lysed with FACS Lysing Solution (Becton-Dickinson) for 10 minutes at room temperature followed by 0.1% sodium azide+PBS Ca++Mg++ free wash. The stained cells were then resuspended in 1 ml of fixing solution (1% paraformaldehyde in PBS, with 0.1% sodium azide). Analysis was accomplished by acquisition of data on a FACScan flow cytometer (Becton-Dickinson) with Cellquest software where at least 20,000 cells were counted per analysis.

Detection of Serum IgG and IgM

Plasma from ALS patient blood was obtained by Percoll gradient centrifugation, and was frozen at −70° C. until use. Standard ELISA for determination of serum antibody:

Anti-Human IgG Fab or anti-Human IgM (Sigma, St. Louis, Mo., USA) were coated (100 mcl/well) into 96-well ELISA plates (Nunc, Roskilde, Denmark) by incubation for at least one hour at 37° C. The plates were washed one time with TBS (150 mM NaCl, mM Tris-HCl, pH7.4), then blocked for 30 minutes by addition of 150 mcl (microliters)/well of BLOTTO (TBS plus 0.1% Tween-20, 2.5% normal goat serum, 2.5% non fat dry milk) at room temperature, with gentle rocking. ELISA plates were subsequently washed once (1×) with TBS. Serial dilutions of serum were added to coated plates (duplicate wells each dilution, 100 mcl/well) and allowed to react for 90 minutes, room temperature. A standard calibration series (0 to 5 mcg/ml) for IgG and IgM (Sigma) was prepared, added to ELISA wells, and incubated in parallel. BLOTTO was used in all dilutions. Following the 90-minute incubation, all fluids were removed by aspiration, then all plates were washed 3× with TBS. Bound IgG antibodies were detected by adding 100 mcl/well of anti-Human IgG alkaline phosphatase-conjugate (Promega Corp., Madison, Wis., USA) diluted 1:10000 in BLOTTO. Bound IgM antibodies were detected by adding 100 mcl/well of anti-Human IgM alkaline phosphatase-conjugate (Kirkegaard & Perry, Gaithersburg, Md., USA) diluted 1:5000 in BLOTTO. Antibody conjugates were incubated for 8one hour at room temperature with gentle agitation. Conjugates were removed by aspiration and plates washed 4× with TBS. Development of color reaction was effected by addition of 100 mcl of PNPP substrate (Sigma) to each well, followed by incubation for 20 minutes at room temperature. The optical density (O.D.) in each well was read at 405 nm. Any sera with exceptionally low or high values were re-tested. Raw IgG and IgM values from ALS samples were multiplied by a conversion factor to account for the different means of preparation from normal plasma.

Statistical Analysis

Cut-off values for defining cell activation as "positive" and "negative" for ALS patients were determined by comparison with values from 37 normal ALS-negative, healthy donors. Results are expressed as the mean±SD. Statistical analysis was performed by GraphPad Prism 4.0 Software (San Diego, Calif., USA), which included two-tailed t-test for two groups' comparison, and One-Way ANOVA (Newman-Keuls test) for analysis of differences between multiple groups. Correlation relationship was analyzed using Pearson's rank correlation coefficient. For all analysis, a value of $P<0.05$ was considered significant.

Example 1

Cross-Section Study of Immune Activation in ALS Patients Compared to Normal Subjects A cross sectional study of immune activation was performed on blood from 40 patients diagnosed with ALS as compared to 37 controls with initial statistical analyses performed independent of drug treatment status. ALS blood cells showed abnormal levels of activation. Table 2 summarizes the results of this study.

TABLE 2

Comparative analysis of serum antibodies and differentiation antigen expression in blood of ALS patients and normal controls

| Parameter | ALS patients (n = 40) | Normal Controls (n = 37[A]) | P Value (ALS vs. Controls) |
|---|---|---|---|
| CD4/CD8 ratio | 2.84 ± 1.53 | 2.20 ± 0.98 | 0.0261 |
| % CD4 | 47.42 ± 8.03 | 37.99 ± 11.96 | <0.0001 |
| % CD4CD38 | 27.14 ± 11.50 | 31.36 ± 10.69 | 0.0799 |
| Med CD4CD38[B] | 12.67 ± 14.24 | 18.83 ± 17.00 | 0.0784 |
| % CD8 | 20.45 ± 8.01 | 19.85 ± 7.05 | 0.6986 |
| % CD8CD38 | 13.35 ± 8.09 | 12.03 ± 4.53 | 0.3620 |
| Med CD8CD38[B] | 3.30 ± 6.32 | 2.68 ± 4.18 | 0.6003 |
| % CD14 | 2.31 ± 0.99 | 3.25 ± 1.41 | 0.0002 |
| Mean CD14DR[C] | 847.79 ± 228.55 | 566.59 ± 130.43 | <0.0001 |
| CD14 SSC | 465.9 ± 155.5 | 388.49 ± 162.24 | 0.0198 |
| % CD14CD16 | 42.44 ± 11.03 | 24.31 ± 15.70 | <0.0001 |
| Serum-IgG (mg/ml) | 8.05 ± 5.72 | 11.26 ± 5.57 | 0.0038 |
| Serum-IgM (mg/ml) | 2.31 ± 2.27 | 1.37 ± 1.14 | 0.0171 |

[A]n = 80 for control samples for serum-IgG and -IgM.
[B]Median CD38 fluorescence expressed on CD4 and CD8 T-Cell.
[C]Mean HLA-DR fluorescence expressed on CD14 monocyte.

Patients with ALS had significantly higher proportional levels of the CD4 T lymphocyte subset as compared to controls ($P<0.0001$). By contrast, the CD8 T cell level was similar in both patients and controls. These proportional differences from control indicate a significant increase in the ratio of CD4/CD8 cells in patients with ALS ($P=0.0261$). No evidence of lymphocytic activation above normal in T cell subsets was observed in patients with ALS.

Compared to controls, the absolute percent of CD14 cells within the total white blood cell count in ALS patient blood was significantly decreased ($P=0.0002$). CD14+ monocytes from patients with ALS expressed significantly higher than normal levels of major histocompatibility (MHC) antigen class II (HLA-DR) ($P<0.0001$) (Table 2). Perivascular macrophages normally constitutively express MHC Class II (HLA-DR), which is upregulated in response to injury (Streit et al. 1989. Expression of Ia antigen on perivascular and microglial cells after sublethal and lethal motor neuron injury. *Exp. Neurol.* 105:115-126). Modulation of HLA-DR on blood monocytes has been associated with a variety of pathogenic states and blood measurements have been shown to have clinical significance (Gascon et al. 2002. Increased HLA-DR expression on peripheral blood monocytes in subsets of subjects with primary HIV infection is associated with elevated CD4 T-cell apoptosis and CD4 T-cell depletion. *J. Acquir. Immune. Defic. Syndr.* 30:146-153; Gu et al. 2003. Time course of proinflammatory and anti-inflammatory responses after cardiac operation: monocyte HLA-DR expression. *Ann. Thorac. Surg.* 76: 654-655; Melichar et al. 2003. Phenotype and antitumor activity of ascitic fluid monocytes in patients with ovarian carcinoma. *Int. J. Gynecol. Cancer.* 13:435-443). Almost half of the CD14 cells in ALS blood had characteristics of tissue macrophages, expressing significantly higher than normal levels of the CD16 antigen ($P<0.0001$).

The aberrant monocytic phenotype defined by higher reactivity for MHC antigen class II (HLA-DR) and CD16 markers, were associated with significant differences in CD14-associated SSC (measure of granularity and differentiation) between patients with ALS and normal controls. Compared with controls, monocytes from ALS patients had statistically increased granularity (higher SSC values) ($P=0.0198$).

Finally, the overall status of humoral immunity was evaluated by quantitating levels of serum-IgG and -IgM in patients with ALS and controls (Table 2); serum-IgG levels in patients with ALS were significantly lower than controls (P=0.0038), whereas, serum-IgM concentrations were significantly higher (P=0.0171).

Example 2

CD4 T-Cell Activation is Decreased in Advanced ALS Disease

To test whether T lymphocytic activation would be related to duration or severity of disease, the T cell activation results were compared with the clinical ALS values shown in Table 1. To simplify clinical correlative analyses, patients were divided into two groups based on the ALSFRS-R scale (0-48, no disease=48). Those with severe impairment (an ALSFRS-R score of 0-24, n=10) were compared to those with milder impairment (ALSFRS-R score >24, n=26).

As shown in FIG. 1, T cell activation levels as quantitated by detection of CD38 antigens on the surface of CD4 T cells was significantly different between the two groups (P<0.05). Compared with controls, CD4/CD38 reactivity was significantly lower in patients with ALSFRS-R score of 24 or lower (P<0.01) whereas no difference of CD4/CD38 reactivity was found in ALS patients with less severe disease (ALSFRS-R score >24). No significant disease associated changes were observed in any of the other T cell (CD4 or CD8) parameters measured.

Example 3

Macrophage Activation and ALS Disease Progression

To evaluate whether systemic monocyte/macrophage activation would be related to duration or severity of disease, macrophage activation parameters from Table 2 were plotted against clinical measures of disease severity to test whether any disease specific changes would be present.

Figure 2A:
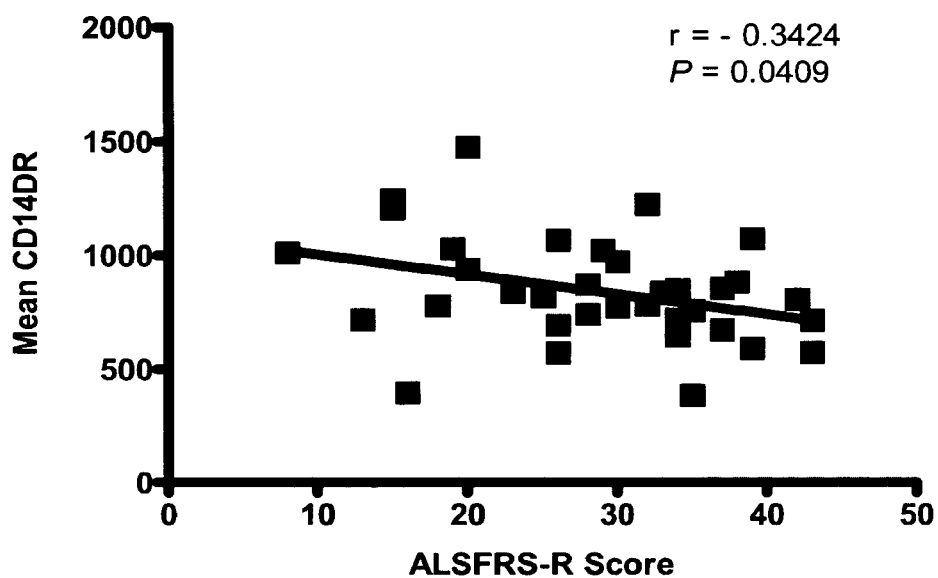

Levels of CD14 cells (as a proportion of total white cell count) did not vary between individuals with mild or severe disease. There was a significant correlation between the level of monocyte/macrophage activation with severity of disease defined by ALSFRS-R score (Pearson r=−0.3464, P=0.0409) (FIG. 2a).

When the rate of ALS disease progression (ALSFRS-R score change per month) was compared to CD14 cell HLA-DR expression, a direct and significant relationship was observed. FIG. 2b shows that higher CD14-DR levels were associated with a more rapid progression of ALS disease (Pearson r=0.3696, P=0.0265). Finally, the elevated level of macrophage differentiation antigen CD16 co-expression on the CD14 expressing monocytes was independent of severity of disease.

Example 4

Changes of Serum-IgG and -IgM in Patients with ALS

Figure 3A:
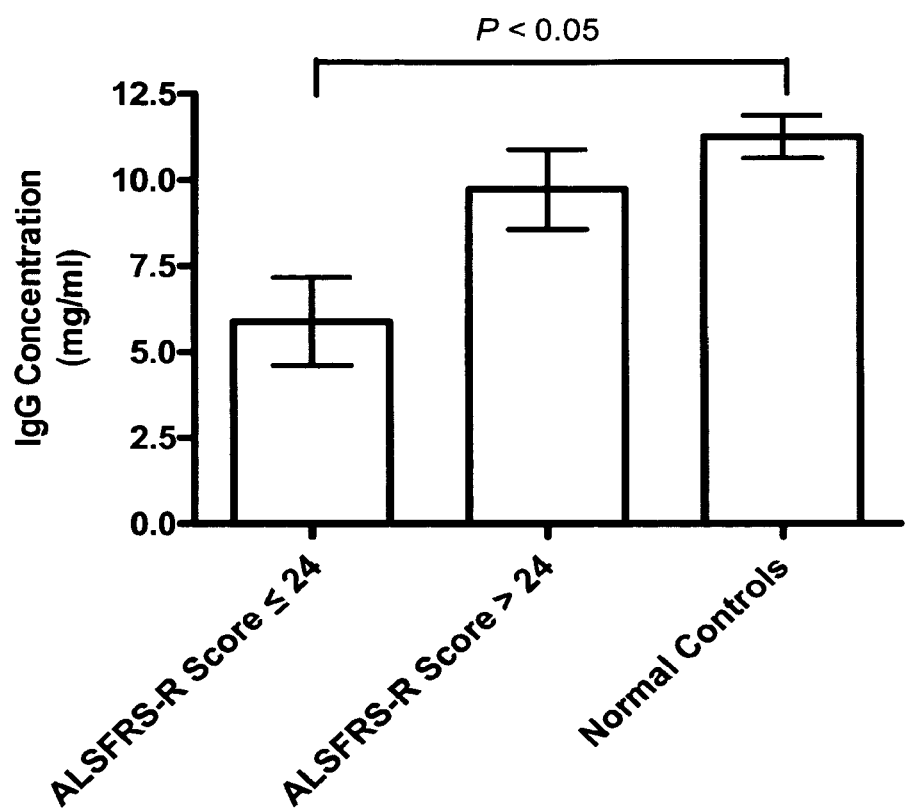
FIGS. 3a-3b are graphs showing a comparison of serum-IgG and -IgM levels between normal controls and ALS patient groups by ALSFRS-R categories.
Figure 3B:
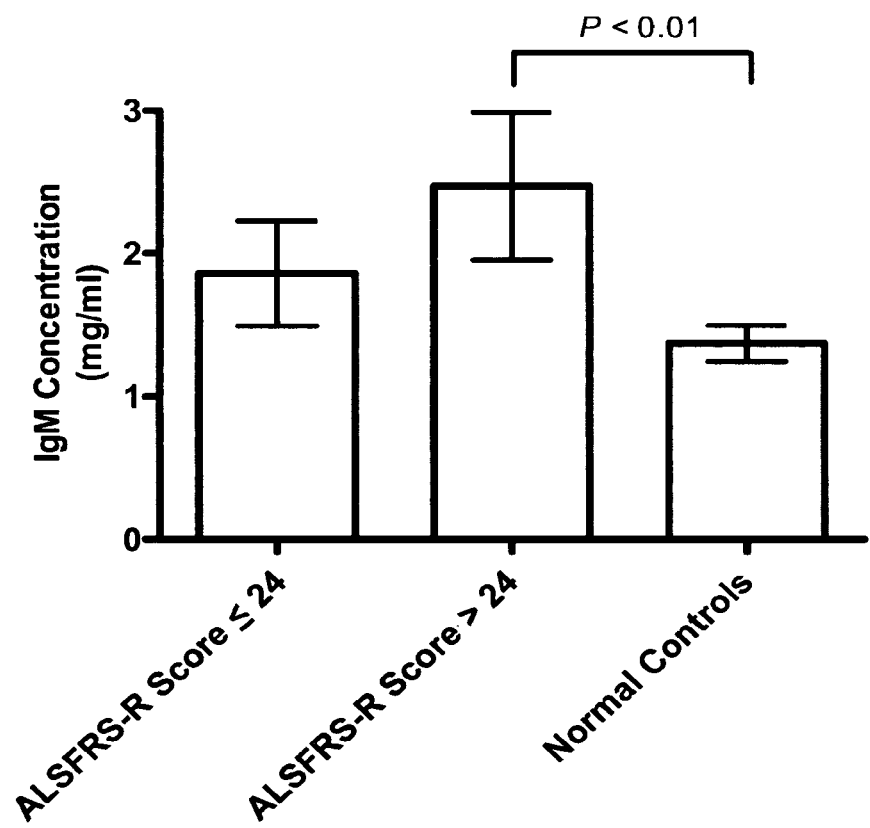

Table 2 shows that the concentration of IgG and IgM in serum was significantly different in patients with ALS as compared to normal controls. Levels of serum-IgG and -IgM also varied with disease severity. ALS patients with ALSFRS-R scores of 0-24 had significantly lower levels of serum-IgG than normal controls (P<0.05) and serum-IgG levels were similar in both individuals with milder disease and controls (FIG. 3a). However, serum-IgM levels were significantly higher in individuals with milder disease (P<0.01) and not significantly different between normal controls and in individuals with severe disease (FIG. 3b).

Example 5

Therapy Related Changes in ALS Specific Immune Activation Status

Table 1 shows the medications that patients with ALS were taking at the time of assessment in the current study. The drugs fell into two different categories; riluzole approved for slowing ALS disease progression and nonsteroidal anti-inflammatory drugs (NSAIDS). Table 3 summarizes the effects of medication treatments on immune activation measurements in patients with ALS. In particular, levels of macrophage activation and differentiation as measured by HLA-DR and CD16 did not change with therapy.

TABLE 3

Comparative analyses of serum antibodies and differentiation antigen expression in blood of normal controls and ALS patients with or without medications

| | ALS patients | | | |
|---|---|---|---|---|
| Parameter | Untreated (n = 6) | riluzole (n = 20) | riluzole + NSAIDS (n = 10) | Normal Controls (n = 37)[A] |
| CD4/CD8 | 2.59 ± 1.46 | 2.77 ± 1.54 | 2.74 ± 1.44 | 2.20 ± 0.98 |
| % CD4 | 44.62 ± 8.09 | 46.10 ± 7.45 | 49.02 ± 9.20 | 37.99 ± 11.96 |
| % CD4CD38 | 20.52 ± 7.92 | 27.88 ± 10.76 | 30.81 ± 14.87 | 31.36 ± 10.69 |
| Med CD4CD38[B] | 5.91 ± 5.47 | 12.76 ± 12.62 | 19.75 ± 20.12 | 18.83 ± 17.00 |
| % CD8 | 21.25 ± 9.59 | 20.20 ± 7.69 | 21.43 ± 8.27 | 19.85 ± 7.05 |
| % CD8CD38 | 15.05 ± 6.70 | 13.20 ± 9.62 | 12.47 ± 5.49 | 12.03 ± 4.53 |
| Med CD8CD38[B] | 2.18 ± 1.99 | 4.90 ± 8.55 | 1.70 ± 2.16 | 2.68 ± 4.18 |
| % CD14 | 2.39 ± 1.10 | 2.28 ± 1.22 | 2.33 ± 0.66 | 3.25 ± 1.14 |
| Mean CD14DR[C] | 779.95 ± 336.69 | 839.02 ± 220.79 | 829.43 ± 181.55 | 566.59 ± 130.43 |
| CD14 SSC | 509.6 ± 220.3 | 457.4 ± 153.2 | 467.2 ± 162.3 | 388.5 ± 162.2 |
| % CD14CD16 | 41.20 ± 8.19 | 44.22 ± 12.91 | 37.83 ± 8.62 | 24.31 ± 15.70 |
| Serum-IgG (mg/ml) | 8.82 ± 5.77 | 7.90 ± 4.58 | 8.59 ± 8.35 | 11.26 ± 5.57 |

TABLE 3-continued

Comparative analyses of serum antibodies and differentiation antigen expression in blood of normal controls and ALS patients with or without medications

| | ALS patients | | | |
| --- | --- | --- | --- | --- |
| Parameter | Untreated (n = 6) | riluzole (n = 20) | riluzole + NSAIDS (n = 10) | Normal Controls (n = 37)[A] |
| Serum-IgM (mg/ml) | 2.48 ± 1.08 | 2.78 ± 3.03 | 1.53 ± 0.87 | 1.37 ± 1.14 |

[A] n = 80 for control samples for serum-IgG and -IgM.
[B] Median CD38 fluorescence expressed on CD4 and CD8 T-Cell.
[C] Mean HLA-DR fluorescence expressed on CD14 monocyte.

Even the inclusion of NSAIDS was not associated with lower levels of macrophage activation (Table 3). Similarly, there were no significant differences between patients in the three treatment categories regarding the levels of CD4/CD38 co-expression and serum-IgG. However dual therapy (riluzole+NSAIDS) was associated with normalization of serum-IgM levels, whereas, the riluzole alone group was no different from untreated patients.

Discussion Relating to Examples 1-5

In the current study, immunophenotypic analyses and humoral immunity assessment was performed on blood from patients with ALS to determine whether systemic immune alteration might be present in ALS. Persistently activated macrophages were observed in the blood of patients with ALS. The high levels of macrophage activation and differentiation were persistent throughout the course of ALS. In addition, macrophage activation defined by CD14 co-expression of HLA-DR became even higher in a disease severity related manner, and was directly related to the rate of disease progression. Moreover, the macrophage activation status was not improved in ALS patients treated by riluzole (the only currently approved treatment for ALS) and NSAIDS. The direct relationship between degree of blood macrophage activation and rate of ALS disease progression indicates a link between the blood and pathogenic processes ongoing in the CNS.

The significantly higher levels of HLA-DR on the circulating monocytes in patients with ALS may be attributed to the reaction of peripheral immune system to motor neuron injury, extending the reaction of microglia/macrophages in the spinal cord and brain in patients with ALS. Alternatively, and as suggested by FIGS. 2a-2b and as observed in HAD and SIVE, activated macrophages in the blood of patients with ALS may communicate with spinal cord perivascular areas and play a direct pathogenic role in disease The high levels of HLA-DR on ALS CD14 cells was coupled with an elevation in the proportion of CD14 cells co-expressing the tissue macrophage marker, CD16 in ALS. CD14+/CD16+ monocytes are a subpopulation of cells that while in the circulation acquire features in common with mature tissue macrophages. They are able to produce proinflammatory cytokines, such as TNFalpha, IL-1alpha, and IL-6, but their expression of the potent antiinflammatory cytokine IL-10 is low or absent. Therefore, CD14+/CD16+ cells may induce more pronounced levels of inflammation than regular monocytes.

CD14+/CD16+ monocytes can rapidly migrate to the site of inflammation, where they readily mature into proinflammatory macrophages. Without being held to theory, neurological disorders such as Alzheimer's disease (AD) and AIDS-related dementia may be due in part to neurotoxic factors released by these cells when migrating into the CNS and crossing the BBB. Elevated levels of HLA-DR expression on CD16 expressing monocytes might result in blood monocytes migrating into the CNS and crossing the BBB in ALS, by mechanisms similar to the activated macrophages in AD and HAD. The decrease of the absolute percent of CD14 cells in patients with ALS may be associated with the migration of circulating CD14/CD16+ cells to perivascular regions of disease, where these cells release local neurotoxic factors such as IL-6, a factor implicated as potentially playing pathogenic roles in ALS (Ono et al. 2001. Increased interleukin-6 of skin and serum in amyotrophic lateral sclerosis. *J. Neurol. Sci.* 187:27-34; Sekizawa et al. 1998. Cerebrospinal fluid interleukin 6 in amyotrophic lateral sclerosis: immunological parameter and comparison with inflammatory and non-inflammatory central nervous system diseases. *J. Neurol. Sci.* 154:194-199), that could damage the motor neurons, similar to AIDS-related dementia and other HIV-associated neurological disorders.

Although blood macrophage abnormalities persisted throughout the pathogenic ALS process in this cross sectional study, T-cell measurements showed changes related to disease severity. Compared with normal controls, ALS patients had a significant increase in T cells expressing CD4, however, the percentage of CD8 T cells was found to be in the normal range, resulting in a significant increase in the ratio of CD4/CD8 cells in ALS. The increased proportions of CD4+ T-cells and the increased CD4/CD8 ratio in the peripheral blood of the ALS patients described herein suggests a possible shift of the immune balance either towards anergy or the Th2 type humoral response rather than a Th1 type cellular immune response. This Th2-like lymphocytic immune response could be induced by the presence of high levels of activated CD14+/CD16+ monocytes in ALS. FcγR (CD16) ligation on activated macrophages may change the phenotype of these activated macrophages to cells that preferentially drive a Th2-like response and result in the alteration of the Th1 type adaptive component of the immune system.

Concentrations of serum-IgG and -IgM antibodies were significantly different compared to normal controls, and also changed with disease progression. Patients with ALS had a normal IgG concentration and higher levels of IgM in early stage of disease. Lower levels of serum-IgG with a concomitant normalization in serum-IgM secretion were observed with disease progression in patients with ALS. Normalization of serum-IgM in ALS patients was associated with combined therapy. The change of serum antibody levels in ALS patient blood might relate to persistent macrophage activation driving CD4 T-cell dysfunction and/or defective Th1 type immunity.

In the study of T cell activation markers, CD38 levels decreased on CD4 T cells with ALS disease progression.

However, the CD8/CD38 reactivity remained within the normal range. These data suggest that the adaptive component of the (T cell) immune system did not become active during ALS pathogenesis. Our observations on blood from patients with ALS suggests that lymphocytes, unlike microglia/macrophages, play a minor role in the active ALS spinal cord associated immune-inflammatory reaction. Therefore, the neuroinflammatory process in ALS may be minimally dependent upon lymphocyte infiltration but rather is driven by macrophage activity.

The inventors have for the first time demonstrated a systemic alteration of blood cell activation in patients with ALS. Persistent disease-associated macrophage activation was observed in ALS blood and levels of HLA-DR on CD14 cells was directly associated with rate of ALS disease progression. The current study confirms systemic macrophage activation in ALS disease, implicating an active role of macrophages in ALS pathogenesis. Abnormally activated macrophages without evidence of concomitant T-cell activation was observed in ALS blood. These observations indicate that systemic immune dysregulation plays a role in the pathogenesis of ALS. The data presented here indicates that ALS may be a kind of systemic inflammatory disease with local manifestations causing motor neuron loss.

These observations are the basis for the methods of the invention for monitoring ALS disease progression, which can be accomplished by measuring the activation- and inflammation-related markers of circulating monocytes, such as HLA-DR and CD16, as well as the status of T-cell activation in patients with ALS. The invention provides valuable assistance in monitoring the treatment of ALS as an immune dysfunction disease. Moreover, These observations are also the basis for the invention as it relates to therapeutic intervention aimed at reducing inflammation in ALS.

Example 6

Treatment of Two ALS Patients with WF10

Two patients, diagnosed with ALS after 2001, received WF10 (also known as IMMUNOKINE™). The drug in each case was used at the same dose with the same interval between doses for each patient. The dose, 0.3 cc/kg, was given intravenously for days as a one hour infusion (0.5 cc/kg of WF10, a 63 mM solution of chlorite containing solution, infused over 1 hour in 500 cc of saline each day for five days). This regimen was repeated every three weeks. One cycle thus was composed of 5 days of 1 hour infusions followed by 3 weeks without receiving drug. Patient 1 received 5 cycles; patient 2 received 4 cycles. No adverse side effects were noted in either patient.

Patient 1 is 59 y.o. woman with a familial form of ALS (a known mutation in the superoxide disniutase gene, SOD) who showed a progressive loss of function as measured by the standard ALS functional rating score (ALS/FRS) from the time of diagnosis (score of 40) until the time of initiation of WF10 therapy 21 months later with a score of 15. In a standard ALS patient, the rate of ALS progression based on the ALS/FRS scoring system is essentially linear, with ALS progressing at a predictable rate after the slope of decline is known. In this case, as well as in the second patient's case, the predicted rate of disease progression is shown as a projected dotted line extending from the solid declination lines in the ALS/FRS scores. At the time of therapy initiation the Patient 1 could no longer swallow food or fluids and had had a gastrointestinal tube (G-tube) placed into her stomach for feeding purposes. The inability to eat is a sign of brain involvement with the degenerative ALS process, whereas the ALS/FRS measurement documents the spinal cord degeneration.

After the first cycle of WF10, the patient had a dramatic improvement of her symptoms, including: restoration of the ability to swallow and eat, leading to the removal of the G-tube (dotted line on the graph denotes time of G-tube placement, the removal is shown as a solid line and after therapy was discontinued, the dotted line shows the placement of a new G-tube), halting of facial fasciculations and vocal waivering (both symptoms of worsening neurologic disease that stopped). During the time of therapy and through 2 months after discontinuation of therapy the ALS/FRS score remained stable at for 7 months, at a time when she would have been predicted to have progressed to a 0 within 5 months absent therapy. She was able to eat by mouth for 8 months after therapy initiation whereas she was never expected to eat after placement of the G-tube. Due to inability to obtain drug after the 5th cycle, she discontinued therapy after 7 months of stable disease and within the next 6 months her ALS disease progressed at a rate identical to her rate pretreatment. Based on the curves shown in FIG. 6, the patient showed a beneficial effect both in the ALS/FRS score of 7 months disease stability and in the reversal of brain based symptoms (bulbar symptoms) of her inability to eat of 8 months. No currently approved or known experimental drug has ever reversed bulbar symptoms and no drug has caused the ALS/FRS score to stabilize.

Figure 6:
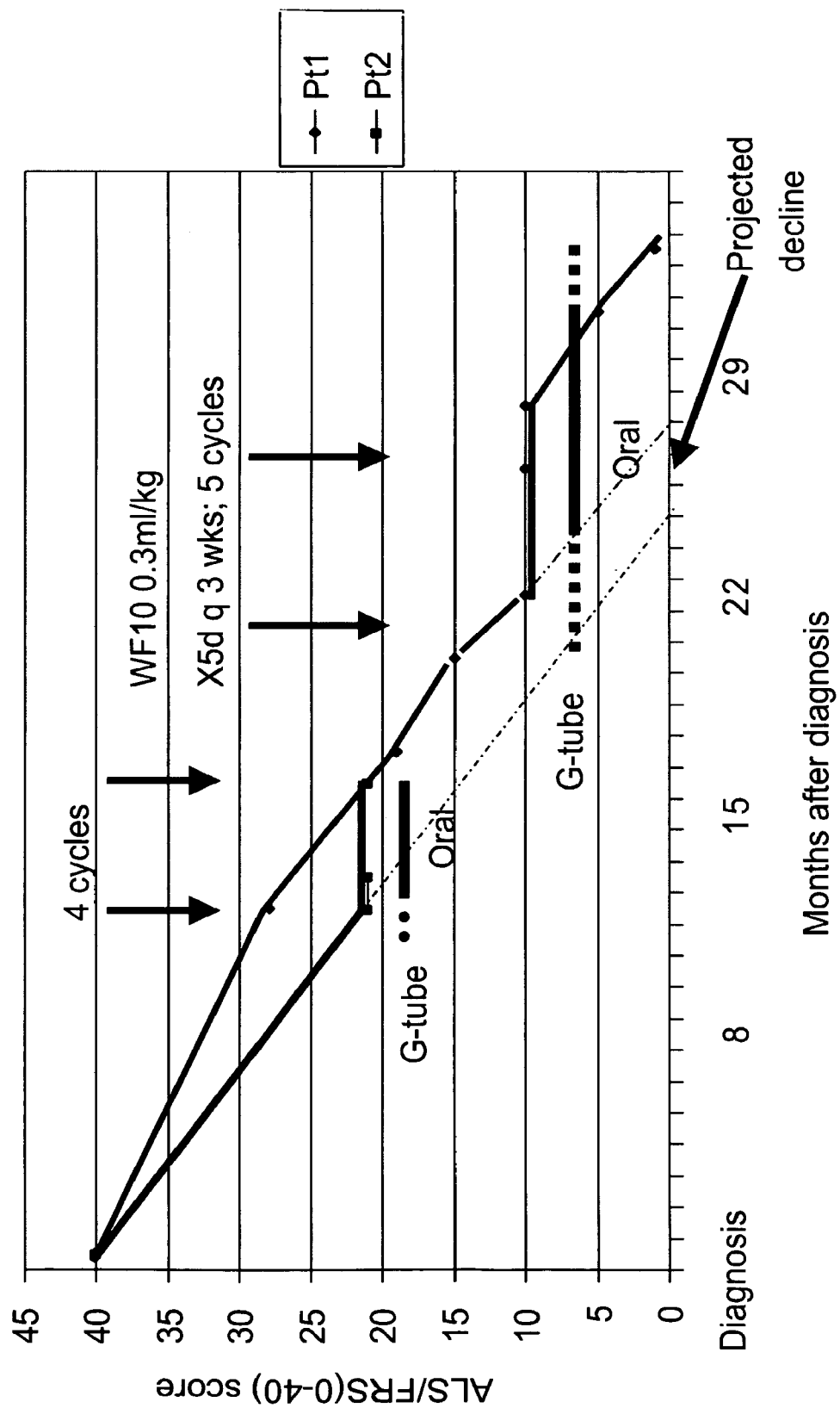
FIG. 6 is a graph showing the results of administration of WF10 to two ALS patients (WF10, 1 cycle=0.3 ml WF10/kg infused over 1 hr, with infusion daily for 5 days, which 5-day regimen was administered once every 3 weeks; data shown at the end of 4 cycles and at the end of 5 cycles. The arrows indicate the periods during which a WF10 cycle was administered. Results are indicated in terms of an ALS/FR (amyotrophic lateral sclerosis/functional) score. G-tube indicates period during which gastric tube was in place. Oral indicates the patient was able to take food by mouth.

Patient 2: This 37 y.o. man, diagnosed with a sporadic (non familial) form of ALS in 2003, had an ALS/FRS score of 40 when diagnosed and within a year had progressed rapidly as shown in FIG. 6. At the time of WF10 therapy he had just had a G-tube placed, as he could no longer swallow. Within a week of WF10 therapy his ability to eat was restored and the G-tube was removed, similar to the clinical response in patient 1. The patient received 4 cycles of WF10 during which his ALS/FRS score remained stable at 21, which allowed him to continue walking with a walker and interacting with his family. His quality of life improved dramatically with initiation of therapy. At the time of patent filing, he has continued to eat and his ALS/FRS score remained at 21, both significant responses lasting for 5 months. As above, no therapy has shown this type of effect.

Figure 4:
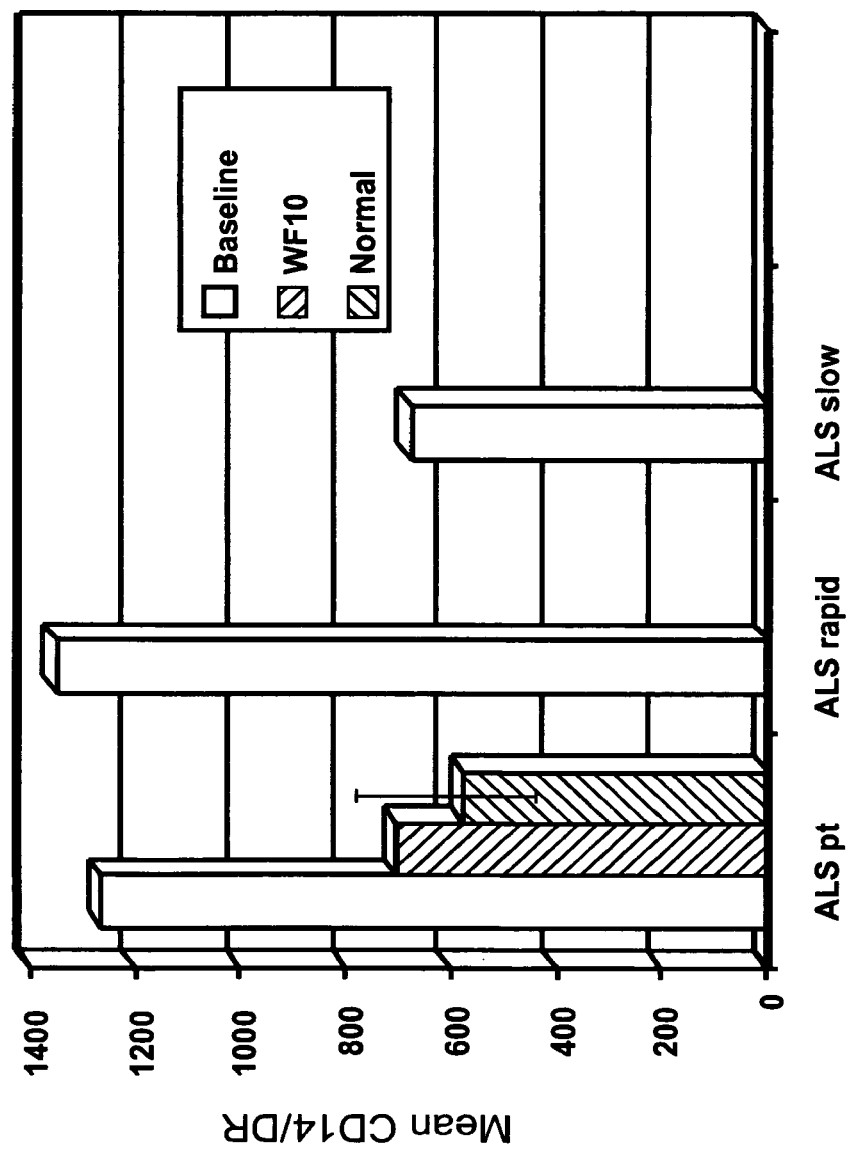
FIG. 4 is a graph showing the effects of WF10 administration upon activated blood macrophages in an ALS patient.

FIG. 4 is shows changes in blood macrophage activation results in Patient 1 as a result of treatment with WF10. The Y axis represents Units of HLA-DR expressed on the surface of blood CD14 cells (monocyte/macrophages). The second column (ALS rapid) shows the level of DR expression exhibited by ALS patients with a rapidly declining clinical course. The third column (ALS slow) shows the level of DR expression in an ALS patient with slowly progressive disease. The progression rates between these two columns differs by approximately 5-10 fold (FIGS. 2a and 2b). The patients with high levels of DR progress 5-10× faster than those with low levels of DR.

The first set of columns in FIG. 4 shows the baseline level of DR (high, fast progressor) in the ALS patient, with the second column representing the level of DR expressed three weeks after one 5 day cycle of WF10 (0.5 cc/kg of WF10, a 63 mM solution of chlorite containing solution, infused over 1 hour in 500 cc of saline each day for three days). The third column in the first set of columns represents the normal (38 normal blood donor composite) level of DR expression on CD14 cells+/−1 standard deviation.

As shown in FIG. 4, the level of HLA-DR on the circulating blood monocytes (CD14+ cells) in Patient 1 was shown to shift from an elevated level to a normal level after one cycle.

Figure 5:
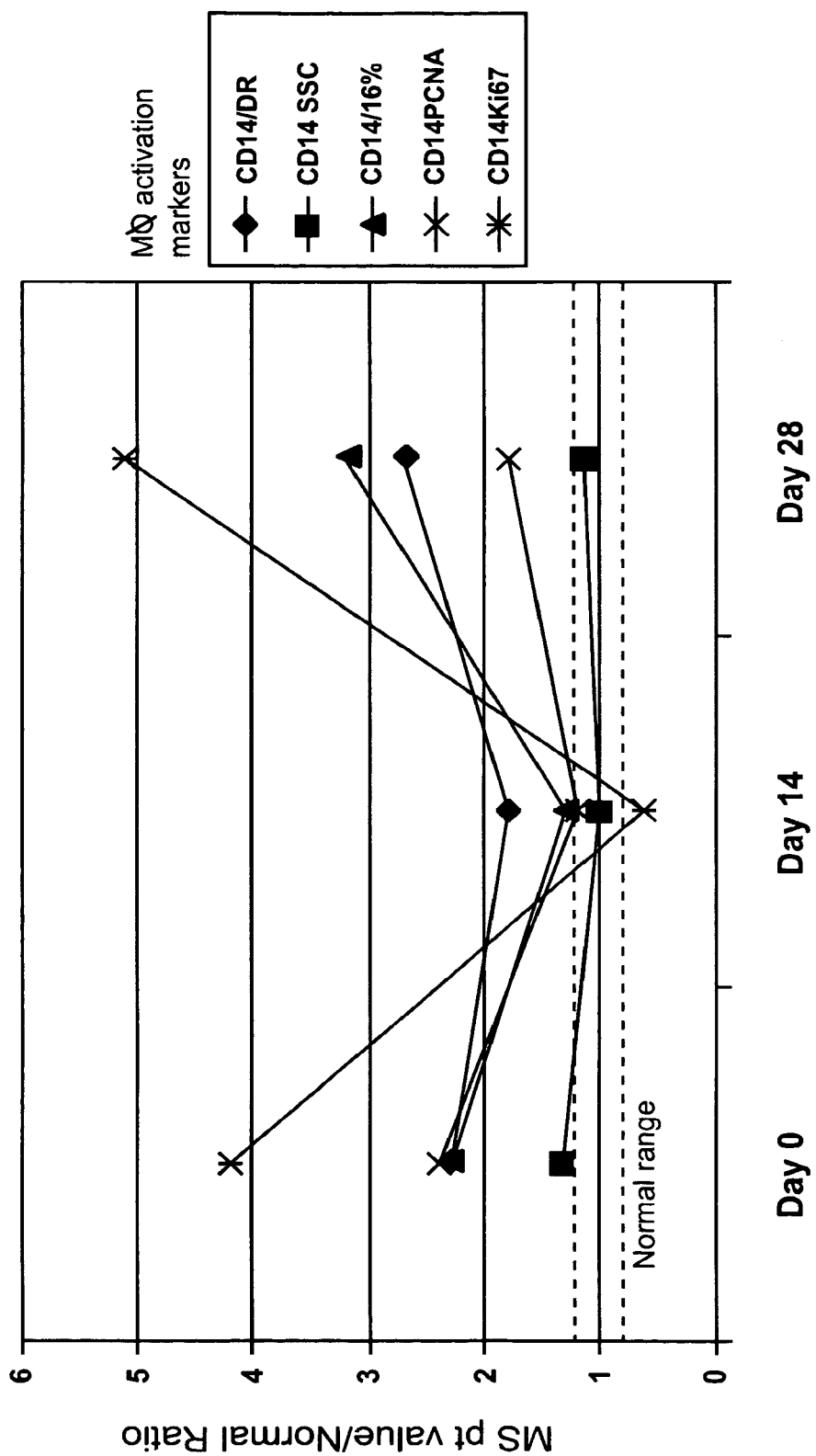
FIG. 5 is a graph of a composite set of curves representing blood macrophage activation measurements taken from a patient with multiple sclerosis treated one cycle of WF10.

In a recent paper (Zhang et al, J NeuroImmunology 2005 159:215-224) the level of DR on monocytes was significantly associated with ALS disease progression rate. The data shown in this figure compare the rates of a rapid progressor with a slow progressor and show that Patient 1's blood monocytes converted from a rapid to a slow phenotype with WF10 administration. This data in conjunction with the clinical data shown in FIG. 6 suggest that the regulation of systemic macrophage activation (also as shown in FIG. 5 for MS) with a chlorite based drug can be monitored by both blood tests and clinical observation.

These data demonstrate that WF10 administration was associated with symptomatic improvement in a rapidly progressing ALS patient at the same time that blood values of macrophage activation resolved, e.g., reduction in pathologic macrophages was concomitant with improvement in the patient.

Example 7

Treatment of Ms Patient with WF10

FIG. 5 is a composite set of curves representing blood macrophage activation measurements taken from a patient with multiple sclerosis (MS) who received WF10 therapy as described in Example 6 above with one cycle of WF10. The values along the Y axis represent the ratio of the observed measurement for each of the parameter measured divided by the normal level (38 normal donor mean value) to yield a ratio. Day 0 represents baseline values for 5 different macrophage activation/proliferation markers. Each of the 5 markers were elevated beyond normal range (shown by the solid and dotted lines) at Day 0.

The patient was then treated with one cycle of WF10 as above and two subsequent blood studies were performed 14 and 28 days after initiation of the 3 day course of WF10. Macrophage proliferation (CD14Ki67, CD14PCNA) and activation (CD14/DR, CD14SSC, CD14/16%) all shifted towards the normal range on day 14 showing a response to one cycle of WF10 in 5/5 macrophage parameters measured. Two weeks later (day 28) the values had essentially returned to pretreatment levels. These data are consistent with a drug induced effect on abnormal macrophage proliferation/activation parameters in a patient with multiple sclerosis.

Example 8

Analysis of Macrophages of ALS and AD Patients

A cross-sectional study of immune activation was performed on blood from 38 patients diagnosed with sALS as compared to control groups with initial statistical analyses performed independent of drug treatment status. In the present investigation two control groups were chosen to compare with sALS patients: 28 age-matched normal controls and 25 AD patients as neurological disease controls. Blood cells from patients with sALS, similar to disease control AD patients, showed abnormal levels of activation. Table 4 summarizes the results of this study. Patients with sALS and AD had significantly higher proportional levels of the CD4 T lymphocyte subset as compared to normal controls ($p<0.05$). By contrast, the CD8 T-cell level and the ratio of CD4/CD8 were similar in all three groups. No evidence of lymphocytic activation above normal in T-cell subsets was observed in patients with sALS and disease controls.

TABLE 4

Comparative analysis of serum antibodies and differentiation antigen expression in blood of sALS patients, normal controls and AD

| Parameter | sALS (n = 38) | Normal Controls (n = 28) | AD (n = 25) | P VALUE (SALS VS. NORMAL) | P VALUE (AD VS. NORMAL) | P Value (sALS vs. AD) |
|---|---|---|---|---|---|---|
| CD4/CD8 | 2.87 ± 1.56 | 2.33 ± 1.59 | 3.43 ± 2.72 | NS | NS | NS |
| % CD4 | 47.43 ± 8.04 | 39.81 ± 11.30 | 47.37 ± 11.22 | <0.01 | <0.05 | NS |
| % CD4CD38 | 27.21 ± 11.76 | 32.24 ± 10.51 | 25.67 ± 12.02 | NS | NS | NS |
| Med CD4CD38 [a] | 13.02 ± 14.54 | 19.15 ± 16.71 | 14.08 ± 16.12 | NS | NS | NS |
| % CD8 | 20.38 ± 8.22 | 21.19 ± 8.53 | 19.93 ± 12.43 | NS | NS | NS |
| % CD8CD38 | 13.67 ± 8.20 | 12.41 ± 6.85 | 15.86 ± 11.46 | NS | NS | NS |
| Med CD8CD38 [a] | 3.43 ± 6.46 | 1.93 ± 2.40 | 5.85 ± 16.19 | NS | NS | NS |
| % CD14 | 2.34 ± 1.01 | 2.51 ± 0.93 | 2.49 ± 1.00 | NS | NS | NS |
| Mean CD14DR [b] | 825.60 ± 206.62 | 582.56 ± 144.35 | 911.93 ± 341.80 | <0.001 | <0.001 | NS |
| CD14 SSC [c] | 466.3 ± 159.6 | 346.5 ± 42.3 | 434.7 ± 226.5 | <0.01 | NS | NS |
| % CD14CD16 | 42.44 ± 11.22 | 23.90 ± 10.60 | 41.77 ± 18.97 | <0.001 | <0.001 | NS |
| Serum-IgG (mg/ml) [d] | 7.80 ± 5.76 | 11.26 ± 5.57 | ND [e] | <0.003 | ND | ND |
| Serum-IgM (mg/ml) [d] | 2.28 ± 2.30 | 1.37 ± 1.14 | ND | <0.03 | ND | ND |

[a] Median CD38 fluorescence expressed on CD4 and CD8 T-Cell.
[b] Mean DR fluorescence expressed on CD14 monocyte.
[c] CD14-associated side light-scatter characteristics.
[d] n = 80 for control samples for serum-IgG and -IgM.
[e] ND, not data Analysis of monocyte/macrophage markers showed that CD14+ monocytes from patients with sALS and AD expressed significantly higher than normal levels of major histocompatibility (MHC) antigen class II (HLA-DR) ($p<0.001$) but no difference was found in the absolute percent of CD14 cells within the total white blood cell count in either of the sALS and AD patient blood specimens as compared to normal controls (Table 4). Almost half of the CD14 cells in sALS and AD blood had characteristics of tissue macrophages, expressing significantly higher than normal levels of the CD16 antigen ($p<0.001$). The aberrant monocytic phenotype defined by higher expression of HLA-DR and CD16 was associated with significant differences in CD14-associated SSC (measure of granularity and differentiation) between patients with sALS and normal controls. Compared with normal controls, monocytes from sALS patients had statistically increased granularity (higher SSC values) (pb0.01). Finally, the overall status of humoral immunity was evaluated by quantitating levels of serum-IgG and -IgM in patients with sALS and normal controls (Table 4); serum-IgG levels in patients with sALS were significantly lower than normal controls ($p<0.003$), whereas, serum-IgM concentrations were significantly higher ($p<0.03$) (sera from the AD patients were not available for study).

The high levels of macrophage activation and differentiation were persistent throughout the course of sALS. In addition, macrophage activation defined by CD14 co-expression of HLA-DR was directly related to the rate of sALS disease progression. Moreover, the macrophage activation status was not improved in sALS patients treated by riluzole (the only currently approved treatment for ALS) or NSAID. The direct relationship between degree of blood macrophage activation and rate of ALS disease progression suggests a link between the blood and pathogenic processes ongoing in the CNS.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method comprising:
    administering chlorite to an individual having amyotrophic lateral sclerosis (ALS);
    obtaining a biological sample from the individual;
    assessing a level of activated monocytes and/or proliferating macrophages in the biological sample obtained from the individual;
    comparing the level of activated monocytes to level of activated monocytes present before the administering, wherein a decrease in the level of activated monocytes after the administering provides an indication that the administering has a positive clinical effect on the individual; and/or
    comparing the level of proliferating macrophages to level of proliferating macrophages present before the administering, wherein a decrease in the level of proliferating macrophages after the administering provides an indication that the administering has a positive clinical effect on the individual; and
    if a positive clinical effect is not observed, adjusting dosage of the chlorite till positive clinical effect is observed.

2. The method of 1, wherein said assessing comprises assessing a level of activated monocytes by measuring one or more markers that indicate monocyte activation, differentiation and/or proliferation.

3. The method of claim 1, wherein said assessing comprises assessing a level of activated monocytes by measuring a level of HLA-DR in a population of CD14+ cells and/or the presence of CD 16+ cells in a population of CD 14+ cells and/or the presence of CD14+/CD16+ cells in said sample.

4. The method of claim 1, wherein said assessing comprises assessing a level of proliferating macrophages by measuring an elevation in proliferation and/or activation markers relative to non-disease blood macrophages.

5. The method of claim 1, further comprising comparing said level of proliferating macrophages to a normal level of proliferating macrophages.

6. The method of claim 1, wherein said chlorite is administered in a form of a matrix of chlorite ions.

7. The method of claim 1, wherein said chlorite is administered in an aqueous formulation.

8. The method of claim 1, wherein said chlorite is administered in a form of a pharmaceutically acceptable chlorite salt.

9. The method of claim 8, wherein said chlorite salt is sodium chlorite.

* * * * *